(12) United States Patent
Gamliel et al.

(10) Patent No.: US 11,771,779 B2
(45) Date of Patent: Oct. 3, 2023

(54) NON-METALLIC MAGNETIC RESONANCE CONTRAST AGENT

(71) Applicant: HADASIT MEDICAL RESEARCH SERVICES & DEVELOPMENT LIMITED, Jerusalem (IL)

(72) Inventors: Ayelet Gamliel, Jerusalem (IL); Talia Harris, Jerusalem (IL); Gal Sapir, Kokhav Yair (IL); Jacob Sosna, Jerusalem (IL); Moshe John Gomori, Jerusalem (IL); Rachel Katz-Brull, Modi'in-Maccabim-Re'ut (IL)

(73) Assignee: HADASIT MEDICAL RESEARCH SERVICES & DEVELOPMENT LIMITED, Jerusalem (IL)

( * ) Notice: Subject to any disclaimer, the term of this patent is extended or adjusted under 35 U.S.C. 154(b) by 181 days.

(21) Appl. No.: 16/964,323

(22) PCT Filed: Jan. 24, 2019

(86) PCT No.: PCT/IL2019/050102
§ 371 (c)(1),
(2) Date: Jul. 23, 2020

(87) PCT Pub. No.: WO2019/145955
PCT Pub. Date: Aug. 1, 2019

(65) Prior Publication Data
US 2020/0345868 A1 Nov. 5, 2020

Related U.S. Application Data

(60) Provisional application No. 62/622,296, filed on Jan. 26, 2018.

(51) Int. Cl.
| | | |
|---|---|---|
| *A61K 49/10* | (2006.01) | |
| *A61B 5/055* | (2006.01) | |
| *G01R 33/56* | (2006.01) | |
| *G01R 33/563* | (2006.01) | |

(52) U.S. Cl.
CPC ............ *A61K 49/10* (2013.01); *A61B 5/055* (2013.01); *G01R 33/5601* (2013.01); *G01R 33/56366* (2013.01)

(58) Field of Classification Search
CPC ........ A61B 5/055; A61K 49/08; A61K 49/10; C07B 59/004; C07F 9/091; G01R 33/56366; G01R 33/5601
See application file for complete search history.

(56) References Cited

U.S. PATENT DOCUMENTS 10,821,194 B2 * 11/2020 Aboagye ............ A61K 51/0402
2005/0281738 A1 * 12/2005 Pettersson .............. A61K 51/00
424/1.11

OTHER PUBLICATIONS

Bertelsen (Magnetic Resonance in Medicine, 2017, 77, p. 1650-1655). (Year: 2017).*
Yang et al., Nuclear Medicine Communications, 2009, 30(6), p. 415-19). (Year: 2009).*
Ramalho et al., J., "Gadolinium-Based Contrast Agent Accumulation and Toxicity: An Update", Am. J. Neuroradiol. 2016, 37, 1192.
Duckett et al., S. B., "Improving NMR and MRI Sensitivity with Parahydrogen", vol. (Ed. L. T. Kuhn), Springer Berlin Heidelberg, Berlin, Heidelberg, 2013, pp. 75-103.
J. H. Ardenkjaer-Larsen, "Increase in signal-to-noise ratio of >10,000 times in liquid-state NMR", Proc. Natl. Acad. Sci. U.S.A. 2003, 100, 10158-10163.
K. Golman, et al., "Molecular imaging with endogenous substances", Proc. Natl. Acad. Sci. U.S.A. 2003, 100, 10435-10439.
Nonaka, H. et al., "A platform for designing hyperpolarized magnetic resonance chemical probes", Nat. Commun. 2013, 4, 2411.
Nonaka, H. et al. "Design of a 15N Molecular Unit to Achieve Long Retention of Hyperpolarized Spin State", Sci. Rep. 2017, 7, 40104.
Abellieri, C. et al. "Therapeutic target metabolism observed using hyperpolarized 15N choline", J. Am. Chem. Soc 2008, 130, 4598-4599.
Jiang Weina et al., "Hyperpolarized 15N-pyridine derivatives as pH-sensitive MRI agents", Scientific Reports (2015).
Kuppusamy, P. et al., "Whole body detection and imaging of nitric oxide generation in mice following" cardiopulmonary arrest: detection of intrinsic nitrosoheme, Magnetic Resonance in Medicine 45:700-707 (2001).
Kanamori, K.: "In vivo N-15 MRS study of glutamate metabolism in the rat brain" Analytical Biochemistry, Anal Biochem. Author manuscript; available in PMC Jul. 1, 20185, pp. 1-36.

* cited by examiner

Primary Examiner — Michael G. Hartley
Assistant Examiner — Leah H Schlientz
(74) Attorney, Agent, or Firm — BROWDY AND NEIMARK, PLLC

(57) ABSTRACT

The present application provides a compound comprising at least one isotopically labeled nitrogen atom for use in diagnosing a condition or disease in a subject, compositions and kits comprising the compound and methods of using the same.

11 Claims, 12 Drawing Sheets

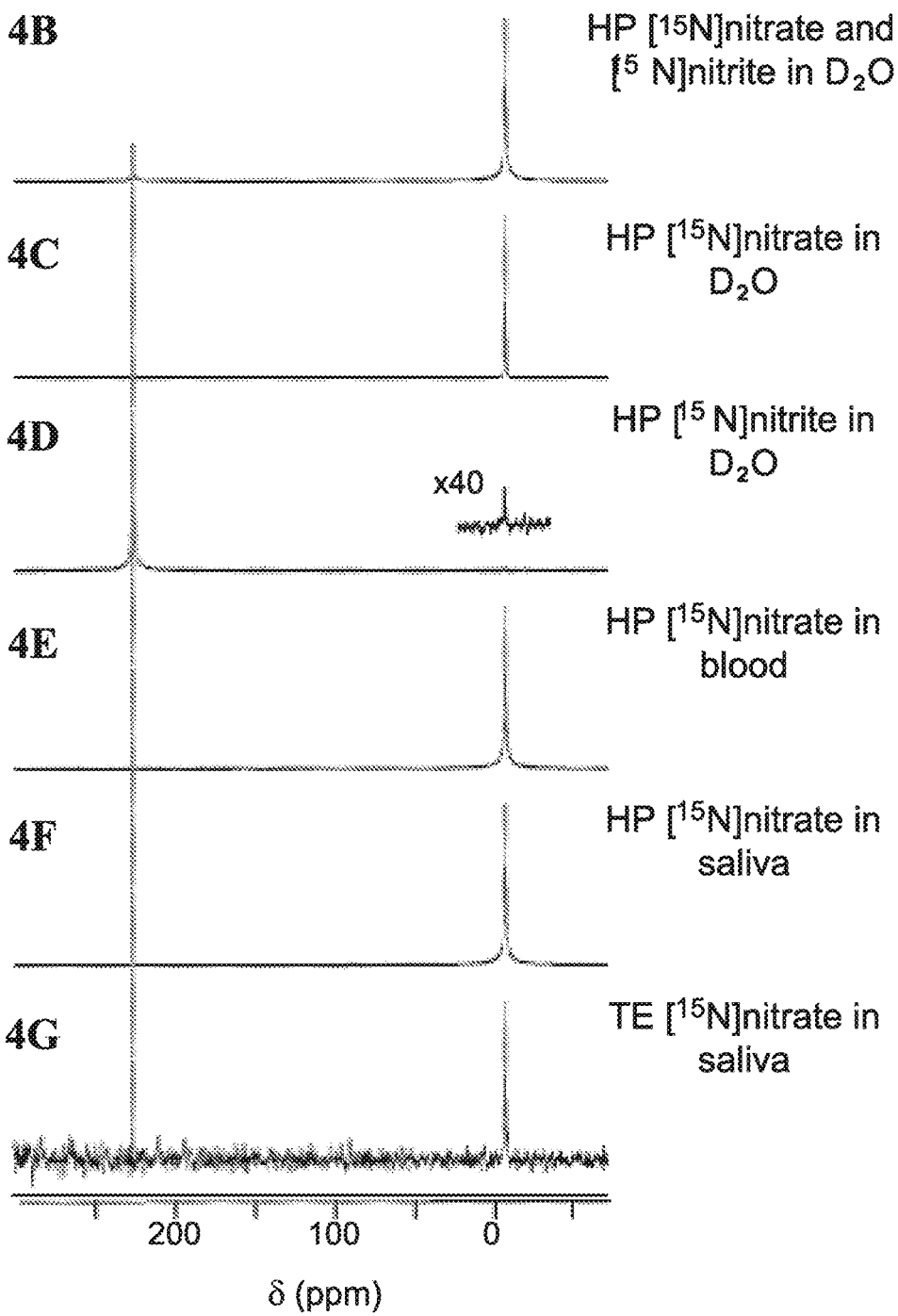

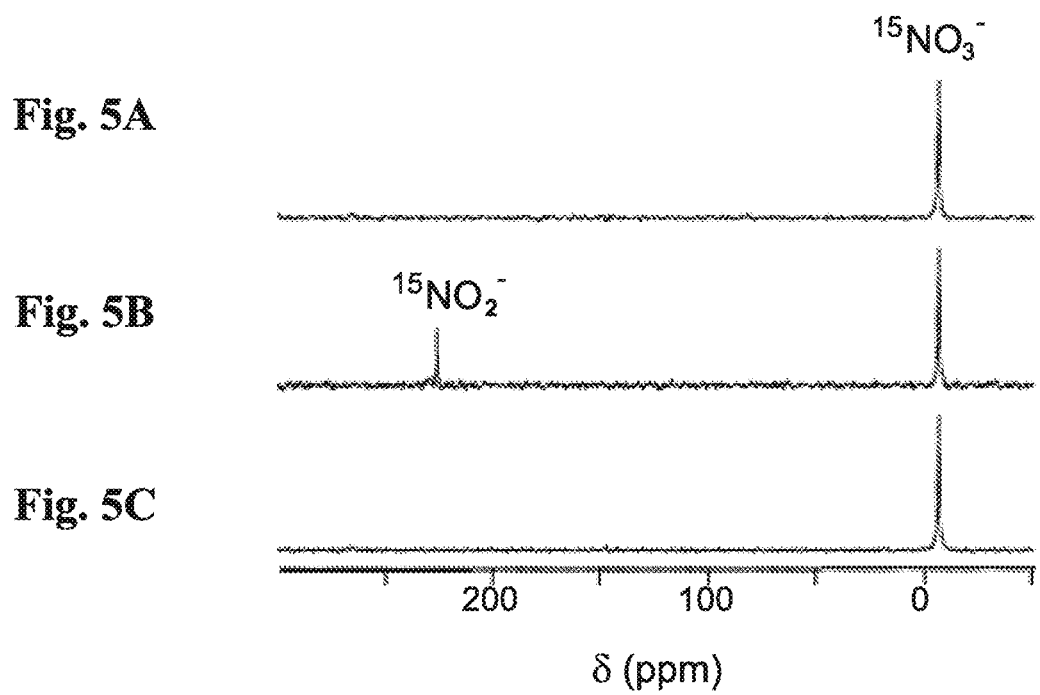
Fig. 5A
Fig. 5B
Fig. 5C
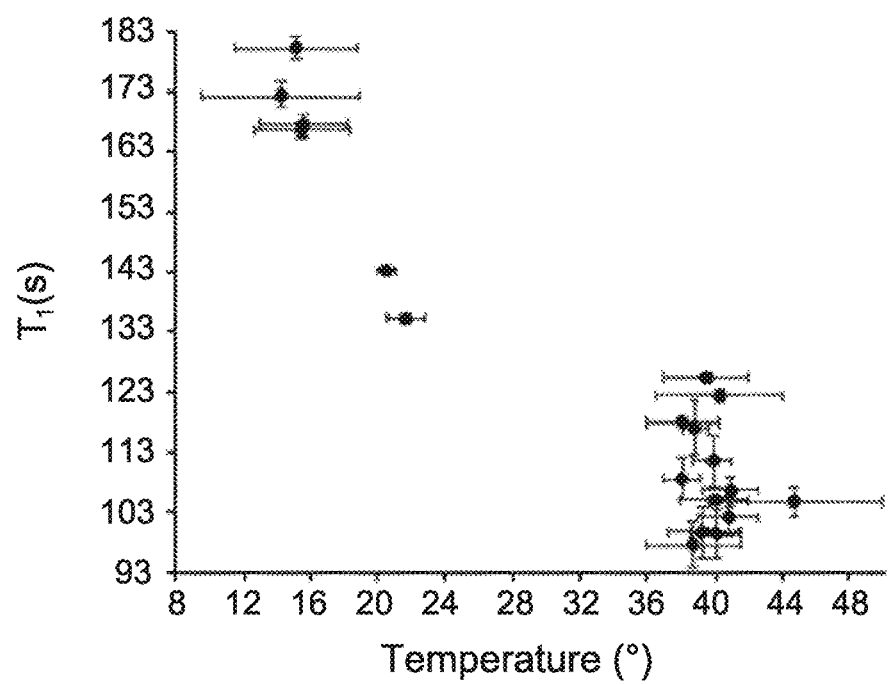
Fig. 6

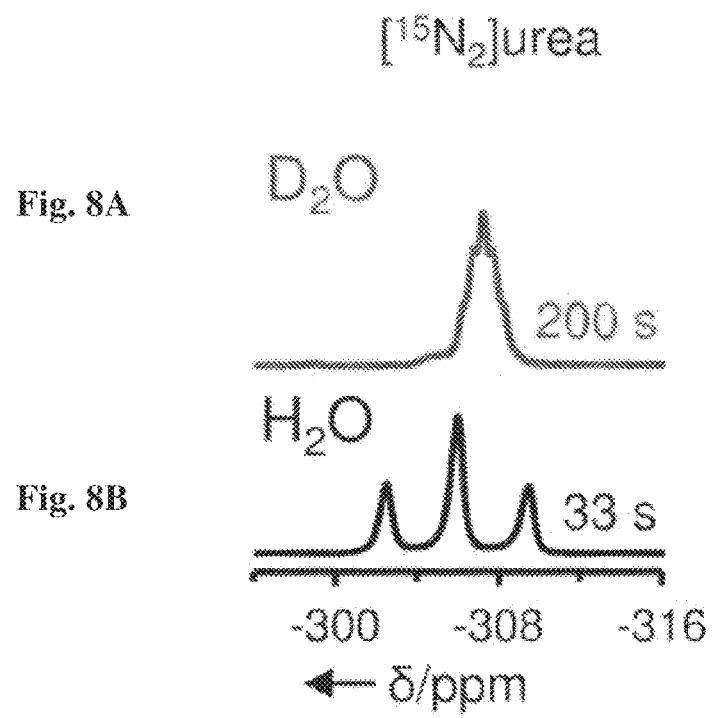
Fig. 8A
Fig. 8B
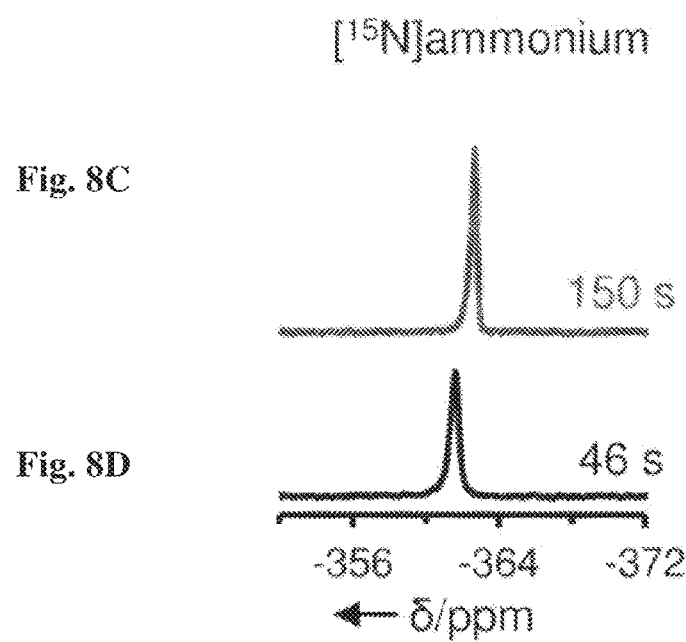
Fig. 8C
Fig. 8D

[$^{15}$N] succinimide 215 s 45 s

⟵ δ/ppm

[guanido-$^{15}$N$_2$]arginine 44 s 6.6 s

⟵ δ/ppm

NON-METALLIC MAGNETIC RESONANCE CONTRAST AGENT

TECHNOLOGICAL FIELD

The present disclosure relates to contrast agents and diagnostic methods for using such agents.

BACKGROUND

Non-invasive diagnosis is highly important and currently involves imaging modalities that rely on nuclear imaging techniques, with the large radiation dose, or perfusion images by magnetic resonance techniques with no radiation, but with administration of lanthanide metal chelates with their potential toxicity [1].

Hyperpolarization techniques such as parahydrogen-induced polarization (PHIP) [2] and dissolution DNP (dDNP) [3] enhance the liquid state nuclear magnetization of small molecules [3]. The enhanced magnetization generated by these methods, however, is not stable and from the moment the polarization transfer process is stopped it will decay back to thermal equilibrium at a rate determined by the longitudinal relaxation time ($T_1$) of the hyperpolarized site. Methods for increasing the $T_1$s were previously reported using $^{13}C$ nucleus [4]. Hyperpolarization of $^{15}N$ labeled compounds has been previously reported [5, 6]

BACKGROUND ART

[1] J. Ramalho, R. C. Semelka, M. Ramalho, R. H. Nunes, M. AlObaidy, M. Castillo *Am. J. Neuroradiol.* 2016, 37, 1192.
[2] S. B. Duckett, R. E. Mewis in *Improving NMR and MRI Sensitivity with Parahydrogen*, Vol. (Ed. L. T. Kuhn), Springer Berlin Heidelberg, Berlin, Heidelberg, 2013, pp. 75-103.
[3] J. H. Ardenkjaer-Larsen, B. Fridlund, A. Gram, G. Hansson, L. Hansson, M. H. Lerche, R. Servin, M. Thaning, K. Golman *Proc. Natl. Acad. Sci. U.S.A.* 2003, 100, 10158-10163.
[4] K. Golman, J. H. Ardenkjaer-Larsen, J. S. Petersson, S. Mansson, I. Leunbach *Proc. Natl. Acad. Sci. U.S.A.* 2003, 100, 10435-10439.
[5] Nonaka, H. et al. *Nat. Commun.* 2013, 4, 2411.
[6] Nonaka, H. et al. *Sci. Rep.* 2017, 7, 40104.

GENERAL DESCRIPTION

The present disclosure provides in accordance with some aspects, a labeled compound comprising at least one isotopically labeled nitrogen atom for use in diagnosing a condition or disease in a subject. In some embodiments, the labeled compound is at least one of an amide, an imide, a nitrogen-containing ion or an amino acid. In some other embodiments, the labeled compound is in a hyperpolarized state.

The present disclosure provides in accordance with some other aspects, a composition comprising a labeled compound comprising at least one isotopically labeled nitrogen atom for use in diagnosing a condition or disease in a subject.

The present disclosure provides in accordance with some further aspects, a kit comprising a labeled compound comprising at least one isotopically labeled nitrogen atom and instructions to use the kit in diagnosing a condition or disease in a subject.

The present disclosure provides in accordance with some further aspects, a method of diagnosis a condition or disease in a subject. The method comprises the steps of administrating to the subject an effective amount of at least one hyperpolarized labeled compound comprising at least one isotopically labeled nitrogen atom and monitoring the hyperpolarized compound in the subject to thereby diagnose the condition or disease in the subject.

The present disclosure provides in accordance with some other aspects, a method of imaging of a subject, the method comprises monitoring a signal from a subject, the subject having been administered with at least one hyperpolarized labeled compound comprising at least one isotopically labeled nitrogen atom.

The present disclosure provides in accordance with some other aspects, a method for imaging at least one body region of a subject, the method comprising administering to the subject an effective amount of at least one hyperpolarized labeled compound comprising at least one isotopically labeled nitrogen atom, and monitoring by imaging the at least one body region.

In some embodiments, monitoring is by Magnetic Resonance (MR) techniques such as Magnetic Resonance Spectroscopy (MRS) and/or Magnetic Resonance Imaging (MRI).

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3B shows T values of hyperpolarized [$^{15}N$]nitrate in solution, at concentrations of 19-29 mM sodium [$^{15}N$]nitrate, *denotes one sample was dissolved in of 4 mL saline solution and another sample was dissolved in 4 mL of saline which were then mixed with 1 mL human saliva, FIG. 3C shows a hyperpolarized signal (HP) of $^{15}N$-nitrate;

FIG. 3D shows a signal of the same sample at thermal equilibrium (TE), All of the spectra were processed with a line broadening of 10 Hz.

FIGS. 4A-4G Hyperpolarized spectra of [$^{15}N$]nitrate and [$^{15}N$]nitrite,

FIG. 4A $^{15}N$ spectra of co-polarized sodium [$^{15}N$]nitrate and sodium [$^{15}N$]nitrite in $D_2O$ (29 mM and 47 mM, respectively), at 37-42° C., the signals of [$^{15}$N]nitrate and [$^{15}$N]nitrite appear at −6.8 and 226.2 ppm, respectively, FIG. 4B A summation of the spectra shown in FIG. 4A, FIG. 4C a summation of the spectra recorded from a hyperpolarized sample of sodium [$^{15}$N]nitrate in D$_2$O (28 mM), at 37-44° C., (a total of 60 spectra with repetition time of 8 s, recorded with a flip angle of 10°), FIG. 4D a summation of the spectra recorded from a hyperpolarized sample of sodium [$^{15}$N]nitrite in D$_2$O (37 mM), at 38-41° C., FIG. 4E a summation of the spectra recorded from a hyperpolarized sample of sodium [$^{15}$N]nitrate (25 mM) in a blood and saline mixture, at 32-36° C., (a total of 48 spectra with repetition time of 5 s, recorded with a flip angle of 10°), FIG. 4F a summation of the spectra recorded from a hyperpolarized sample of sodium [$^{15}$N]nitrate (18 mM) in a saliva and saline mixture, at 37-42° C., (a total of 82 spectra with repetition time of 5 s, recorded with a flip angle of 10°), FIG. 4G a summation of thermal equilibrium spectra of sodium [$^{15}$N]nitrate (18 mM) in a saliva and saline mixture (same sample as in FIG. 4F), HP-hyperpolarized; TE-thermal equilibrium.

FIGS. 5A-5C $^{15}$N-NMR long term monitoring of [$^{15}$N] nitrate metabolism in saline and in saline-saliva solution, FIG. 5A a solution containing sodium [$^{15}$N]nitrate (22 mM) and glucose (2.7 mM) in saline, scanned for 5 days, FIG. 5B a solution containing 3 mL of the solution in FIG. 5A combined with 0.75 mL of human saliva, scanned for 5 days, the ratio of the [$^{15}$N]nitrite to [$^{15}$N]nitrate integrals is about 3:10, FIG. 5C the same solution as in FIG. 5A, scanned for 5 days, the scan started after 14 days at room temperature.

FIG. 6 The dependence of the $^{15}$N T$_1$ of sodium [$^{15}$N] nitrate on temperature, solutions of sodium [$^{15}$N]nitrate at 29 mM in D$_2$O were used, the temperature was monitored online with an MRI compatible temperature sensor, for each point—the X-axis error bar represents the temperature range in which the T$_1$ was determined, and the Y-axis error bar represents the 95% confidence interval for the individual fit (see Methods), the data points shown here in the range of 34-50° C. are also summarized in FIG. 3B.

FIG. 7B shows an online temperature recording of the sample in the spectrometer, FIG. 7C shows the signal intensities of the hyperpolarized site in the consecutive injections, * indicates that the intensities are shown normalized to the highest signal for each injection.

FIGS. 8A-8H $^{15}$N NMR spectra showing the hyperpolarized signal of $^{15}$N sites upon dissolution in H$_2$O (lower traces) and D$_2$O (upper traces), FIGS. 8A and 8B are $^{15}$N spectra of [$^{15}$N$_2$]urea dissolved in D$_2$O and H$_2$O, respectively, FIGS. 8C and 8D are $^{15}$N spectra of [$^{15}$N]ammonium dissolved in D$_2$O and H$_2$O, respectively, FIGS. 8E and 8F are $^{15}$N spectra of [$^{15}$N]succinimide dissolved in D$_2$O and H$_2$O, respectively, FIGS. 8G and 8H are $^{15}$N spectra of [$^{15}$N][guanido-$^{15}$N$_2$] arginine dissolved in D$_2$O and H$_2$O, respectively, all spectra were acquired with a 10° excitation angle without $^1$H or $^2$H decoupling at 35-40° C. in a 5.8 T magnet.

FIG. 9A decay of hyperpolarized [$^{15}$N$_2$]urea signal when dissolved in D$_2$O (Δ), H$_2$O (◇), or a small volume dissolved in D$_2$O added to whole blood (•), all at 37° C., The integrals are corrected for the effect of repeated excitations to allow a straightforward comparison of the different signals acquired with different acquisition parameters, FIG. 9B shows repeated injections of hyperpolarized urea to blood.

FIG. 10A a typical experiment showing simultaneous monitoring of the temperature (upper panel) and the $^{15}$N signal integral (lower panel) of a hyperpolarized $^{15}$N$_2$ urea solution in D$_2$O, $^{15}$N signal integrals were binned by 10° C. segments (indicated by alternating shading) and the T$_1$ of each segment was determined (inset), FIG. 10B shows T$_1$ of hyperpolarized [$^{15}$N$_2$]urea dissolved in D$_2$O at different temperatures, the superscripts indicate how many measurements were used for each temperature range. a: n=3, b: n=4, c: n=5, the data were analyzed with a two-tailed t-test and significant differences are marked as follows: **=p<0.005, *=p<0.05.

DETAILED DESCRIPTION OF EMBODIMENTS

Figure 1:
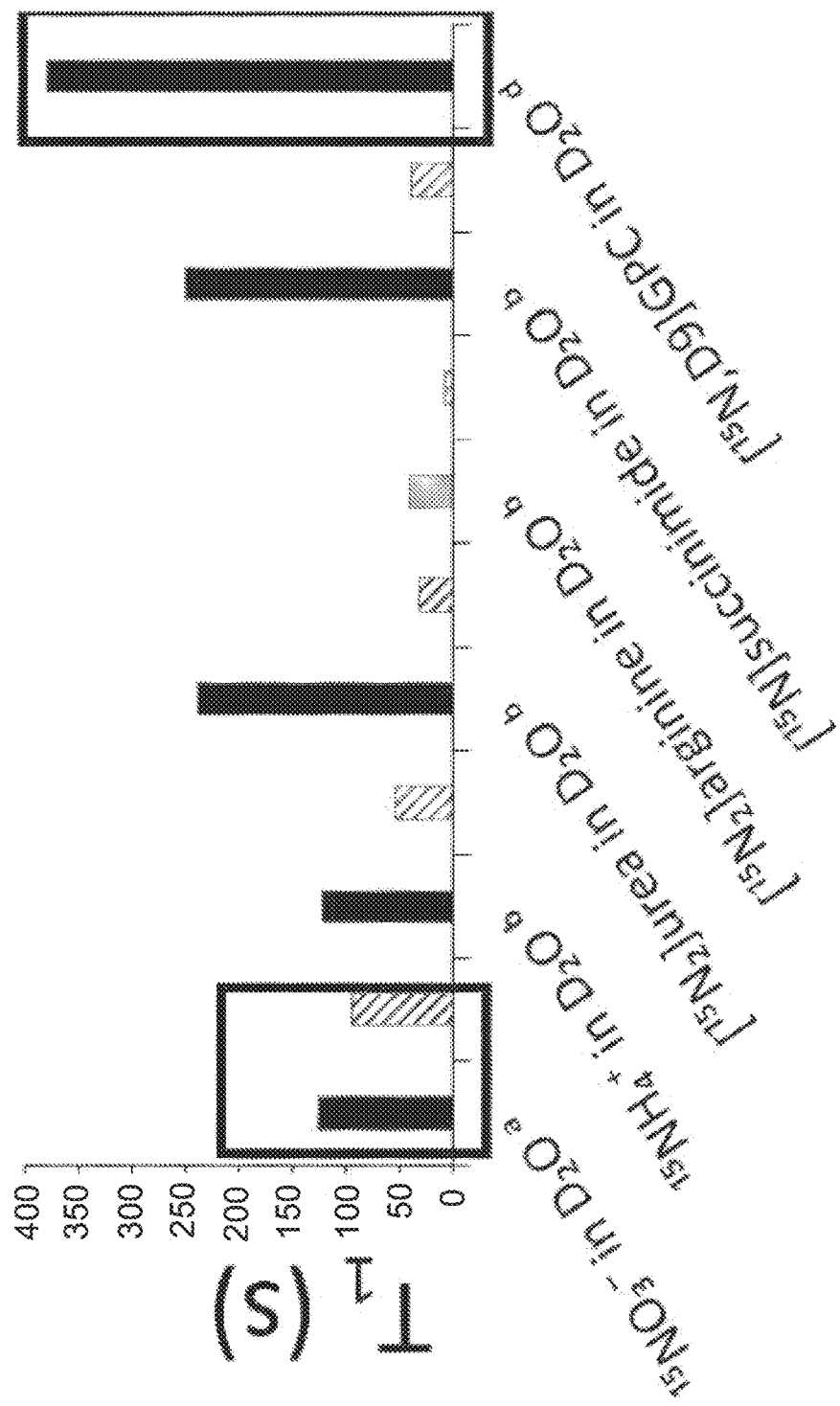
FIG. 1 $^{15}N$ $T_1$s of selected molecules in water ($H_2O$) and $D_2O$ measured at 5.8 T; (a) denotes $Na^{15}NO_3$; (b) denotes solid-state polarization in $D_2O$ and dissolution in $D_2O$.; (c) denotes solid-state polarization in $D_2O$ and dissolution in $H_2O$.; In this case, during the decay in solution the nitrogen positions are fully protonated as confirmed by the respective split pattern of the signal (not shown); a, b, and c—determined experimentally; (d) denotes estimation.

Diagnosis of a disease is highly important as it may assist in identifying the disease and it's progression as well as treatment regimen and follow-ups means. Imaging techniques such as positron emission tomography (PET), computed tomography (CT) and magnetic resonance imaging (MRI), are often used for diagnosis of a variety of disease/ condition. While PET and CT involve X-rays or the use of ionizing radiation, MRI is a safe non-invasive imaging method. MRI diagnosis is based on metal chelates, such as gadolinium (Gd) chelates as a contrast agent, which safety has been recently questioned.

Thus, there is a need to develop non-toxic agents that can be safely administered and used in diagnosis using non-invasive magnetic resonance (MR) methods such as Magnetic Resonance Spectroscopy (MRS) and/or MRI.

The present disclosure is based on the development of compounds, labeled with a stable, non-radioactive, nitrogen isotope, $^{15}$N (denoted herein as "labeled compound"), that are in hyperpolarized state. These compounds are, on one hand, metal free, safe to use and have no ionization energy and on the other hand, experience an increased detection signal and hence can provide an increased diagnostic accuracy.

Based on these unique features, the inventors suggested that the labeled hyperpolarized compounds may be promising safe candidates for diagnosis purposes of various diseases and conditions.

As shown in the Examples below, the compounds developed herein are characterized by long MR relaxation times and are suitable in diagnosis of malignancies, for example, in breast cancer.

Thus, the present disclosure refers to compounds labeled with one or more N-15 atom being in hyperpolarized state, to compositions and kits comprising the compounds and to methods of using such compounds, composition or kits for imaging and diagnostic purposes, optionally by using MR methods.

Unless otherwise stated, the term labeled compound, refers to a compound labeled with one or more (at least one) N-15 atom. The present disclosure also encompasses these labeled compounds, which are optionally, labeled with one or more additional atom, such as hydrogen atom.

In accordance with the first aspect, the preset disclosure provides a labeled compound comprising one or more isotopically labeled nitrogen atom for use in diagnosing a condition or disease in a subject.

The term "isotopically labeled atom" is meant to encompass an atom in a compound of the invention for which at least one of its nuclei has an atomic mass which is different than the atomic mass of the prevalent naturally abundant isotope of the same atom. Due to different number of neutrons in the nuclei, the atomic mass of a isotopically labeled atoms is different. The total number of neutrons and protons in the nucleus represents its isotopic number.

The labeled compound as used herein may be also denoted as an $^{15}$N-containing compound.

When referring to isotopically labeling of a nitrogen atom (herein "isotopically labeled nitrogen" or "labeled nitrogen"), it should be understood to relate to a $^{15}$N isotope of nitrogen. Natural nitrogen has two stable (non-radioactive) isotopes, nitrogen-14 (N-14), which represents the majority of naturally occurring nitrogen, and nitrogen-15 (N-15 or $^{15}$N), which is less common. Each of N-14 or N-15 has 7 protons, N-14 has 7 neutrons and N-15 has 8 neutrons.

In some embodiments an isotopically labeled atom is $^{15}$N (having 8 neutrons and 7 protons in nitrogen nucleus). As will be appreciated by the description below, the isotopic labeling of specific atoms in a compound of the invention is achieved by techniques known to a person skilled in the art of the invention, such as for example synthesizing compounds of the invention from isotopically labeled reactants or isotopically enriching specific nuclei of a compound.

$^{15}$N is characterized by having a fractional nuclear spin of one-half. Two sources of nitrogen-15 are the positron emission of oxygen-15 and the beta decay of carbon-15. When the compound includes an $^{15}$N atom, it replaces one or more of the N-14 atoms present in the compound.

When referring to a compound comprising at least one isotopically labeled atom, it should be understood to encompass compound having isotopically labeled atoms above the natural abundance of the at least one isotopically labeled atom. In some other embodiments, for compounds having $^{15}$N isotopically labeled atom, the isotopically enrichment of the nitrogen in a specific position in a compound of the invention, may be is between about 0.37% to about 99.9%. Thus, a compound or a composition as described herein may have different degrees of enrichment of isotopically labeled atoms.

It should be noted that in the context of the present disclosure, the term isotope labeling (or isotopically labeling of an atom) does not refer to a radioactive labeling. In other words, radioactive labeling of atoms in the compounds described herein is excluded from the present disclosure.

The present disclosure thus encompasses compounds that comprise at least one labeled nitrogen atom. It should be noted that the terminology referring to "at least one labeled nitrogen atom" or "one or more labeled nitrogen atom" is to be understood as a compound having one or more of it's nitrogen atoms labeled.

In some embodiments, the compound comprises at least one labeled nitrogen atom, at times at least two labeled nitrogen atom, at times even at least three labeled nitrogen atom. In some embodiments, the compound comprises one, two, three, four or more $^1$N atoms.

In some embodiments, the compound is or comprises at least one of an amine, an amide, an imide, a nitrogen-containing ion or an amino acid.

In some embodiments, the compound is or comprises an amine. An amine group can be classified according to the nature and number of substituents on nitrogen atom. Aliphatic amines contain only hydrogen (H) and alkyl substituents. Aromatic amines have the nitrogen atom connected to an aromatic ring. A Primary (1) amines comprises two hydrogen atoms and one organic substituent (an alkyl or aromatic group)bound to the nitrogen atom, secondary (2) amines have two organic substituents (alkyl, aryl or both) bound to the nitrogen together with one hydrogen, tertiary (3) amines has the nitrogen atom bound to three organic substituents. Quaternary ammonium salts exist with many kinds of anions.

In some embodiments, the compound is or comprises at least one of a primary amine, a secondary amine or a tertiary amine. In some embodiments, the compound is or comprises at least one of a primary amine, a secondary amine or a tertiary amine, an amide, an imide, a nitrogen-containing ion or an amino acid.

In some embodiments, the compound is or comprises at least one of an amide, an imide, a nitrogen-containing ion or an amino acid.

In some embodiments, the compound is or comprises an amino acid. The present disclosure encompasses all natural and synthetic amino acids. In some embodiments, the amino acid is arginine.

In some embodiments, the compound is at least one of an amide, a nitrogen-containing ion or an imide.

In some embodiments, the compound is or comprises an imide. In some embodiments, the compound is or comprises succinimide.

In some embodiments, the compound is a nitrogen-containing ion. The nitrogen-containing ion as used herein refers to a nitrogen atom being a negatively charged atom or a positively charged atom.

In some embodiments, the compound is or comprises at least one of ammonium, guanidinium, succinimide or glycerophosphocholine (GPC).

In some embodiments, the compound is or comprises an ammonium ion. In some embodiments, the compound is or comprises a guanidinium group. In some embodiments, the compound is glycerophosphocholine (GPC).

In some embodiments, the compound is or comprises a nitrate group or a nitrite group. In some embodiments, the compound is [$^{15}$N]nitrate. The compound [$^{15}$N]nitrate is to be understood as having the chemical structure of $^{15}NO_3^{-1}$. The [$^{15}$N]nitrate may be in a salt form, optionally as a sodium salt. In some embodiments, the compound is sodium nitrate ($NaNO_3$).

In some embodiments, the compound is or comprises an amide. In some embodiments, the compound is urea. In some embodiments, at least one of the nitrogen atoms is labeled with a nitrogen atom and thus the compound is [$^{15}$N]urea. In some embodiments, two of the nitrogen atoms are labeled with a nitrogen atom and thus the compound is [$^{15}N_2$]urea.

The compound [$^{15}$N]urea is to be understood as having one of the two nitrogen atoms labeled with N-15 and having the chemical structure of $^{15}NH_2C(=O)NH_2$ and the compound [$^{15}N_2$]urea is to be understood as having both nitrogen atoms labeled with N-15 and having the chemical structure of $(^{15}NH_2)_2C(=O)$.

The labeled compound described herein may comprise, an additional isotopically labeled atom, further to the labeled nitrogen atom. In some embodiments, the compound comprises at least one isotopically labeled hydrogen atom, $^2$H (having 1 neutron and 1 proton in hydrogen nucleus). In the context of the present disclosure, when referring to a isotopically labeled hydrogen atom or a labeled hydrogen it should be understood to relate to a deuterated hydrogen atom (deuterium or "D"). Deuterium is the stable isotope of hydrogen, which includes in its nucleus one proton and one neutron. When the compound includes a deuterium atom, it replaces one or more of the hydrogen atoms present in the compound.

In some embodiments when the isotopically labeled atom is deuterium, the isotopically enrichment of the deuterium in a specific position in a compound of the invention, may be between about 0.015% to about 99.9%.

In some embodiments, the at least one isotopically labeled nitrogen atom may be directly bonded to the at least one isotopically labeled hydrogen atom. In other embodiments the at last one isotopically labeled nitrogen atom may be adjacent (on a neighboring atom) to said at least one isotopically labeled hydrogen atom.

In some embodiments, the compound is [$^{15}$N]urea or [$^{15}$N$_2$]urea having at least one labeled hydrogen. In some embodiments, the compound is [$^{15}$ND]urea. In some embodiments, the compound is [$^{15}$ND$_2$]urea. In some embodiments, the compound is [$^{15}$ND$_3$]urea. In some embodiments, the compound is [$^{15}$ND$_4$]urea.

In some embodiments, the compound is [$^{15}$N$_2$D]urea. In some embodiments, the compound is [$^{15}$N$_2$D$_2$]urea. In some embodiments, the compound is [$^{15}$N$_2$D$_3$]urea. In some embodiments, the compound is [$^{15}$N$_2$D$_4$]urea.

In some embodiments, the compound is [$^{15}$N]urea, [$^{15}$N$_2$]urea, [$^{15}$ND]urea, [$^{15}$ND$_2$], [$^{15}$ND$_3$], [$^{15}$ND$_4$], [$^{15}$N$_2$D], [$^{15}$N$_2$D$_2$], [$^{15}$N$_2$D$_3$], [$^{15}$N$_2$D$_4$] or any combination thereof.

In some embodiments, the compound is [$^{15}$ND]urea, [$^{15}$ND$_2$], [$^{15}$ND$_3$], [$^{15}$ND$_4$], [$^{15}$N$_2$D], [$^{15}$N$_2$D$_2$], [$^{15}$N$_2$D$_3$], [$^{15}$N$_2$D$_4$] or any combination thereof.

In some embodiments, the compounds of the present disclosure are in the hyperpolarized state. As described herein, a compound undergoes hyperpolarization being in a solid state, e.g. at low temperatures for example as low as 1K or 2° K and may undergo a subsequent dissolution within a solution, while still in a hyperpolarized state.

Accordingly, the term hyperpolarized state encompasses a compound being in a solid state form or in a liquid form. In some embodiments, the labeled compounds of the present disclosure are in the hyperpolarized state within a solution. In some embodiments, the labeled compounds of the present disclosure are in the hyperpolarized state within an aqueous solution. As described herein, the aqueous solution may comprise D$_2$O.

The term hyperpolarized state as used herein should be understood in the context of magnetic resonance (MR) techniques.

A signal obtained in an MR technique for particular nucleus is a results of a difference in the spin population energy level of this nucleus. The strength/intensity of the MRR signal depends on the difference in the numbers of nuclei at the low energy level and at the high energy level. The difference between the population of a nucleus at high and low nuclear energy levels is the "polarization" of the nuclei. Under thermal equilibrium conditions, the polarization is relatively low thereby resulting in a weak signal at MR techniques.

When referring to hyperpolarization of the compound of the present disclosure, it should be understood to relate to a compound wherein some of its atoms' spin polarization is increased. The term hyperpolarized state as used herein refers to a state of the nitrogen nuclear spins and specifically to a change in the N-15 spin distribution resulting with an over-population of spins in the low energy state (increased spin polarization). Thus, increasing the polarization of a specific nucleus in a compound consequently creating an artificial, non-equilibrium distribution of the spin population of a nucleus, i.e. a "hyperpolarized" state, where the spin population difference is increased by several orders of magnitudes compared with the thermal equilibrium.

There are several methods for increasing nuclear spin polarization. The methods are applied to compounds of the invention ex vivo, and subsequently administered, similar to contrast agents, although with as biomarkers. The dynamic nuclear polarization (DNP) method is one of the most widespread due to its versatility, as it can be applied to a wide variety of molecules. DNP operates on the principle of the Nuclear Overhauser Effect (NOE). The current dissolution DNP method performs spin polarization transfer at low temperatures, where the electron spins have very high polarization levels. During the polarization transfer, the target molecule and an electron donor molecule are maintained as an amorphous solid that is then rapidly dissolved just before use. This method regularly achieves polarization on the order of 20% to 40% (e.g. compared with approximately 0.00008% polarization for $^{13}$C per Tesla at body temperature).

In parahydrogen-induced polarization (PHIP), spin polarization is transferred from parahydrogen to the target molecule via a chemical reaction. The process can be accomplished rapidly, yielding high levels of polarization, but due to the requirements of the chemical reaction, only a limited set of molecules can be polarized using this technique.

The increased spin polarization changes several features of the labeled compounds described herein as compared to the corresponding compound in a non-hyperpolarized state, including increasing the signal observed in MR. Thus, in accordance with some embodiments, the labeled compounds described herein, when being in a hyperpolarized state, are characterized by an increased MR signal as compared to the labeled compounds in a non-hyperpolarized state.

In some embodiments, the compound described herein are in a hyperpolarized state. In some embodiments, the compound is at least one of hyperpolarized N-15 labeled ammonium, hyperpolarized N-15 labeled guanidinium, hyperpolarized N-15 labeled succinimide or hyperpolarized N-15 labeled glycerophosphocholine (GPC).

In some embodiments, the compound is a hyperpolarized [$^{15}$N]nitrate or [$^{15}$N]nitrite. Surprisingly, the inventors have found that salts of nitrate and specifically sodium salt can safely undergo a process of hyperpolarization and dissolution (e.g. forming solid state at cryo temperatures and dissolution at temperatures above 0° C.) and be used as a contrast agent.

In some embodiments, the compound is a hyperpolarized [$^{15}$N]nitrate. In some embodiments, the hyperpolarized [$^{15}$N]nitrate is in a liquid form. In some embodiments, the compound is a hyperpolarized Na[$^{15}$N]nitrate, optionally in a liquid form.

In some embodiments, the compound is hyperpolarized N-15 labeled urea. In some embodiments, the hyperpolarized N-15 labeled urea is in a liquid form.

In some embodiments, the compound is hyperpolarized [$^{15}$N]urea. In some embodiments, the compound is hyperpolarized [$^{15}$N$_2$]urea. In some embodiments, the hyperpolarized compound is [$^{15}$ND]urea, [$^{15}$ND$_2$]urea, [$^{15}$ND$_3$]urea, [$^{15}$ND$_4$]urea, [$^{15}$N$_2$D]urea, [$^{15}$N$_2$D$_2$]urea, [$^{15}$N$_2$D$_3$]urea, [$^{15}$N$_2$D$_4$]urea or any combination thereof. In some embodiments, the hyperpolarized compound is [$^{15}$N]urea, [$^{15}$N$_2$]urea, [$^{15}$ND]urea, [$^{15}$ND$_2$]urea, [$^{15}$ND$_3$]urea, [$^{15}$ND$_4$]urea,

[$^{15}$N$_2$D]urea, [$^{15}$N$_2$D$_2$]urea, [$^{15}$N$_2$D$_3$]urea, [$^{15}$N$_2$D$_4$]urea or any combination thereof. In some embodiments, such hyperpolarized compound are in a liquid form.

In some embodiments, the hyperpolarized labeled compound is characterized by an $^{15}$N MRS signal that has increased signal by at least 1,000 compared to the MRS signal of the same compound in a non-hyperpolarized state measured at the same magnetic field.

In some other embodiments, the hyperpolarized labeled compound is characterized by an $^{15}$N MRS signal that has increased signal of between 1,000 to 10,000 compared to the MRS signal of the same compound in a non-hyperpolarized state at the same magnetic field, at times between 1,000 to 5,000. The increased signal may be denoted as enhancement factor.

As appreciated, the increased $^{15}$N MRS signal of the hyperpolarized labeled compound as compared to the $^{15}$N MRS signal of the same labeled compound in a non-hyperpolarized state can be determined the acquiring $^{15}$N spectra under conditions, for example, as shown in the Examples herein below.

In some embodiments, the hyperpolarized labeled compound is characterized by an $^{15}$N MRS signal that has at least 1% to 50% increased polarization compared to the MRS signal of the same compound in a non-hyperpolarized state. In some other embodiments, the hyperpolarized labeled compound is characterized by an $^{15}$N MRS signal that has at least 5% to 30% increased polarization compared to the MRS signal of the same compound in a non-hyperpolarized state. The increased polarization can be determined from the enhancement factor as known to a skilled person in the field, for example of dissolution dNTP.

This increase in MR signal is a highly important advantage enabling the use of the hyperpolarized labeled compound described herein for diagnostic purposes. An additional advantage of the hyperpolarized labeled compound relate to their effective lifetime that determines the time period at which the spin polarization is maintained. In other words, the time period at which the compound carries the increased signal can be detected by MR.

The effective lifetime of the compound is dictated by the compound's relaxation. In MR techniques (MRS, MRI), the term relaxation describes how signals change with time. In general signals deteriorate with time, becoming weaker and broader. The deterioration reflects the fact that the MR signal, which results from nuclear magnetization, arises from the over-population of an excited state. Relaxation is the conversion of this non-equilibrium population to a normal population. In other words, relaxation describes how quickly spins "forget" the direction in which they are oriented. The deterioration of an MR signal is analyzed in terms of two separate processes, each with their own time constants. One process, associated with $T_1$, is responsible for the loss of signal intensity. Thus, the effective lifetime of the compound is dictated by the compound's T relaxation. This time, $T_1$ determines how much spin polarization is lost. Thus, as detailed herein, in order to maintain an increased signal, the hyperpolarized compound is prepared just before it's use in MR, to minimize relaxation losses.

Nitrogen atoms that directly bound to hydrogen atoms may have low $T_1$ values. For example, ammonium ions and primary amines in amino acids may show a $T_1$ value of several tens of seconds, however their visibility is very sensitive to pH changes and other microenvironment parameters, due to the changes in the exchange rate of the protons on the amines. The same rational can be followed for any other nitrogen bonded to exchangeable protons.

The inventors have surprisingly found that it is possible to use compounds having N-15 directly bound to hydrogen atoms and managed to prolong the compound's $T_1$—by exchanging the protons with deuterons. This is done by preparing the formulation for solid-state polarization in D$_2$O or by using D$_2$O in the dissolution solvent as a small amounts of D$_2$O in the blood are not toxic. In this way it has been found by the inventors to dramatically increase the visibility window of $^{15}$N-labeled compounds such as ammonium chloride, urea, arginine, and succinimide.

In some embodiments, the compound has a $T_1$ relaxation of a $^{15}$N nucleus of at least about 30 seconds. In some embodiments, the hyperpolarized label compound has a $T_1$ relaxation of a $^{15}$N nucleus of between 30 seconds to 600 seconds In some other embodiments, the hyperpolarized label compound has a $T_1$ relaxation of a $^{15}$N nucleus of between 50 seconds to 380 seconds. In some other embodiments, the hyperpolarized label compound has a $T_1$ relaxation of a $^{15}$N nucleus of between 50 seconds to 200 seconds. As appreciated, the $T_1$ relaxation may depend on the temperature at which it is measured.

In some embodiments, the compound is [$^{15}$N]nitrate, optionally Na[$^{15}$N]nitrate, in a hyperpolarized state having a $T_1$ relaxation of a $^{15}$N nucleus of at least 90 seconds, at least 100 seconds, even at least 150 seconds or between 100 seconds to 200 seconds.

In some embodiments, the compound is [$^{15}$N]nitrate, optionally Na[$^{15}$N]nitrate, in a hyperpolarized state having a $T_1$ relaxation of a $^{15}$N nucleus of between 100 seconds to about 115 seconds measured at a temperature of between about 34° C. to about 50° C.

In some embodiments, the compound is [$^{15}$N]nitrate, optionally Na[$^{15}$N]nitrate, in a hyperpolarized state having a $T_1$ relaxation of a $^{15}$N nucleus of about 109 seconds measured at a human body temperature of between about 34° C. to about 44° C.

In some embodiments, the compound is [$^{15}$N]nitrate, optionally Na[$^{15}$N]nitrate, in a hyperpolarized state having a $T_1$ relaxation of a $^{15}$N nucleus of about 105 seconds measured at a temperature of between about 40° C. to about 50° C.

In some embodiments, the compound is [$^{15}$N]nitrate, optionally Na[$^{15}$N]nitrate, in a hyperpolarized state having a $T_1$ relaxation of a $^{15}$N nucleus of about 170 seconds measured at a temperature of between about 10° C. to about 20° C.

In some embodiments, the compound is [$^{15}$N]urea having at least one labeled hydrogen atom in a hyperpolarized state having a $T_1$ relaxation of a $^{15}$N nucleus of at least 150 seconds, at least 200 seconds, at least 250 seconds, at least 300 seconds, even at least 350 seconds or between 100 seconds to 400 seconds. In some embodiments, the compound is [$^{15}$N]urea, [$^{15}$N$_2$]urea, [$^{15}$ND]urea, [$^{15}$ND$_2$], [$^{15}$ND$_3$], [$^{15}$ND$_4$], [$^{15}$N$_2$D], [$^{15}$N$_2$D$_2$], [$^{15}$N$_2$D$_3$], [$^{15}$N$_2$D$_4$] or any combination thereof in a hyperpolarized state having a $T_1$ relaxation of a $^{15}$N nucleus of 380 seconds measured at a temperature of between about 65° C. to about 75° C.

The compound of the present disclosure may be used in the form of a composition or a kit. Thus, the present disclosure further provides a composition comprising at least one labeled and hyperpolarized compound detailed herein. It is noted that the composition may comprise at least one compound of the invention in a mixture with pharmaceutically acceptable auxiliaries, and optionally other therapeutic agents. The auxiliaries must be "acceptable" in the sense of being compatible with the other ingredients of the composition and not deleterious to the recipients thereof.

In some embodiment, the composition comprising $D_2O$. The amount of $D_2O$ in the composition depends on a variety of factors. In some embodiments, the composition comprising the labeled hyperpolarized compound comprises between 10 ml to 20 ml.

Compositions and compounds of the invention may be administrated by any known method in the art. These include, but are not limited to, injection (e.g., using a subcutaneous, intramuscular, intravenous, or intradermal injection), dermal, intranasal administration and oral administration. The amount of a compound according to the invention that may be used in a formulation of the invention, or generally administered to a subject, may be determined by the practitioner to provide an effective diagnosis, e.g., imaging. As compounds of the invention are non-toxic, the amount or dosage selected may be such to yield an effective end result.

Compositions administrable to a subject include those suitable for oral, rectal, nasal, topical (including transdermal, buccal, and sublingual), vaginal or parenteral (including subcutaneous, intramuscular, intravenous, and intradermal) administration or administration via an implant. The compositions may be prepared by any method well known in the art of pharmacy. Such methods include the step of bringing in association a compound of the invention with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents.

Compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The present disclosure further provides a composition, as hereinbefore described, in combination with packaging material, including instructions for the use of the composition for diagnosis as detailed herein. For parenteral administration, suitable compositions include aqueous and non-aqueous sterile injection. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulizers or insufflators.

The present disclosure further provides a kit comprising at least one compound of the invention comprising at least one isotopically labeled nitrogen, in a hyperpolarized state, and means for administering the at least one compound and instructions for use.

In accordance with some further aspects, the preset disclosure provides a compound as described herein comprising at least one labeled nitrogen and being in a hyperpolarized state, a composition comprising the compound or a kit comprising the compound for use in diagnosis a condition or a disease in a subject.

The term "diagnosing a condition or disease" is meant to encompass any process of investigating, identifying, recognizing, assessing a condition, disease or disorder of the mammalian body, including all tissues and structures in the body (for example blood vessels). A diagnosis according to the present disclosure using a compound described herein includes, but is not limited to objective quantitative diagnosis of a condition or disease, prognosis of a condition or disease, genetic predisposition of a subject to have a condition or disease, efficacy of treatment of a therapeutic agent administered to a subject (either continually or intermittently), quantification of neuronal function, diagnosis and evaluation from the fields of oncology, neurology, psychiatry, cardiology, vascular, infection and inflammation of a therapeutic agent activity, determination of drug efficacy, characterization of masses, tumors, cysts, blood vessel abnormalities, and internal organ function; quantification of brain, kidney, liver, and other organs' metabolic function; examination of the action, response or progress of therapy (involving medicinal and non-medicinal treatment) aimed at alleviating or curing at least one of oncology, neurology, psychiatry, cardiology, vascular, infection and inflammation diseases and disorders.

In some embodiments, the disease or condition is at least one of a malignant disease, an inflammatory disease or a vascular diseases.

In some embodiments, the disease or condition is a proliferative disorder.

A proliferative disorder, diagnosed by utilizing compounds of the invention, is a disorder displaying cell division and growth that is not part of normal cellular turnover, metabolism, growth, or propagation of the whole organism. Unwanted proliferation of cells is seen in tumors and other pathological proliferation of cells, does not serve normal function, and for the most part will continue unbridled at a growth rate exceeding that of cells of a normal tissue in the absence of outside intervention. A pathological state that ensues because of the unwanted proliferation of cells is referred herein as a "hyper-proliferative disease" or "hyper-proliferative disorder." It should be noted that the term "proliferative disorder", "cancer", "tumor" and "malignancy" all relate equivalently to a hyperplasia of a tissue or organ.

Non-limiting examples of cancers include blastoma, carcinoma, lymphoma, leukemia, sarcoma, mesothelioma, glioma, germinoma, choriocarcinoma, melanoma, glioblastoma, lymphoid malignancies, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In some embodiments, the disease or condition is breast cancer. In some embodiments, the disease or condition is hepatocellular carcinoma. In some embodiments, the disease or condition is a metastatic tumour in the lungs.

In some embodiments, the disease or condition is an inflammatory disorder.

An inflammatory disorder, diagnosed by utilizing compounds of the invention, is a disorder encompassing any immune response. The inflammatory disorder may be an infectious or a non-infectious disorder. Non-infectious inflammatory disorders are any disorder which the activation of macrophages or activated macrophages play a role such as auto-immune disorders and inflammatory disorders which are not infection related, i.e. non-pathogenic, caused by other than an infectious agent (e.g. auto-antigen, hypersensitivity, wound). Not limiting examples include inflammatory diseases of the gastrointestinal tract such as Crohn's disease, inflammatory bowel disease, gastritis, colitis, ulcerative colitis, colon irritable, gastric ulcer and duodenal ulcer, inflammatory diseases of the skin such as psoriasis, inflammatory diseases of the respiratory system such as asthma, allergic rhinitis or chronic obstructive pulmonary disease (COPD), pulmonary fibrosis, sarcoidosis, inflammatory diseases of the musculoskeletal system such as rheumatoid arthritis, osteomyelitis, osteoporosis, or neuritis, systemic sclerosis, inflammatory diseases of the kidneys such as glomerulonephritis, renal ischemia, or renal inflammation; inflammatory diseases of the nervous system such as multiple sclerosis, Alzheimer's disease and HIV-1-associated dementia; autoimmune diseases such as diabetes, type 1 and 2 diabetes mellitus and graft versus host reaction; infectious disease such as nephritis, sepsis, septic shock, endotoxic shock, adult respiratory distress syndrome; inflammatory conditions of the cardiovascular system, such as myocardial infarction, myocarditis, atherosclerosis, hypertensive cardiomyopathy, atheroma, intimal hyperplasia or restenosis or autoimmune disorders such as Multiple Sclerosis (MS), inflammatory arthritis, rheumatoid arthritis (RA).

In some embodiments, the disease or condition relates to the differentiation of inflammation from oedema in inflammatory processes.

In some embodiments, the disease or condition is multiple sclerosis (MS) and the use is for proper stage identification of MS.

In some embodiments, the disease or condition is a cardiovascular disease (CVD). CVD is a class of diseases that involve the heart or blood vessels. In some embodiments, the cardiovascular diseases is coronary artery diseases (CAD), stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, and venous thrombosis. Examples of CAD include stable angina, unstable angina, myocardial infarction (commonly known as a heart attack), and sudden cardiac death.

The compounds can be used for perfusion imaging, also denoted as perfusion MRI or perfusion-weighted imaging (PWI). Perfusion imaging is perfusion scanning by the use of a particular MRI sequence. The acquired data are then post processed to obtain perfusion maps with different parameters, such as BV (blood volume), BF (blood flow), MTT (mean transit time) and TTP (time to peak). In some embodiments, the In some embodiments, the disease or condition is associated with poor blood circulation. In accordance with such embodiments, the compound of the invention may be used in Myocardial perfusion imaging (MPI). MPI is indicative on how well blood flows through (perfuses) through the heart muscle and can show regions of the heart muscle that are not well perfused, i.e. are not getting enough blood flow.

In some other embodiments, the disease or condition is selected from the following non-limiting list: peripheral artery disease (PAD), blood clot, varicose veins, diabetes, obesity, Raynaud's disease or a proliferative disorder.

In some embodiments, the disease or condition is a stroke. A stroke is known as a medical condition in which poor blood flow to the brain results in cell death.

In some embodiments, the disease or condition is a central nervous system disease.

The compound, composition or kit according with the invention are all possibly utilized in a variety of applications: in acquiring a magnetic resonance spectrum of a subject or a region of a subject, acquiring a magnetic resonance image of a subject or the region, in diagnosing a condition or disease in a subject and others.

In accordance with another aspect, the present disclosure thus provides a method of imaging of a subject, the method comprises monitoring a signal from a subject using an imaging or a spectroscopic method, the subject having been administered at least one compound according to the invention.

It should be noted that monitoring a signal encompasses collecting data possibly in a form of an image or a spectrum from a subject including any region of the subject body. The term "monitoring" as used herein is meant to encompass the quantitative and/or qualitative detection and observation of a signal originating from the hyperpolarized compound of the invention being administered to the subject.

In another aspect, the invention provides a method for imaging at least one body region of a subject, the method comprising administering to the subject an effective amount of a compound according to the invention, and imaging the at least one body region.

As noted herein, compounds of the invention are suitable for imaging and diagnosis. Diagnosis is required for the identification of specific subjects (sub-population) suffering from a specific disorder or condition.

In some embodiments, the method of the invention is utilized for determining a site of a disease or condition and/or for distinguishing between healthy and abnormal tissues or organs. In some embodiments, the method is used for distinguishing or differentiating between malignant and benign tumors.

In a further aspect, the invention provides a method for diagnosis of a disease or condition in a subject, the method comprising administering to the subject a diagnostically effective amount of a compound according to the invention, and monitoring the subject or a body region of the subject to thereby identify body regions susceptible of having a disease or a condition.

In another aspect the invention provides a method for diagnosing a condition or disease in a subject, said method comprising:
  administrating to the subject a diagnostically effective amount of a hyperpolarized labeled compound comprising at least one isotopically labeled nitrogen atom;
  monitoring the hyperpolarized compound, thereby diagnosing the condition or disease in the subject.

In some embodiments, the method comprising prior to administration, a step of hyperpolarizing the compound comprising at least one isotopically labeled nitrogen atom.

In another aspect the invention provides a method for diagnosing a condition or disease in a subject, said method comprising:
  hyperpolarizing a compound comprising at least one isotopically labeled nitrogen atom;
  administrating to the subject an effective amount of the hyperpolarized compound;
  monitoring the hyperpolarized compound, thereby diagnosing the condition or disease in the subject.

The hyperpolarization may be conducted at a temperature between 1° K to 2° K to obtain a solid state hyperpolarized compound. The hyperpolarization step may be performed using various techniques. For example, the hyperpolarization may be performed using dynamic nuclear polarization techniques at a temperature between 1° K to 2° K. Further for example, the hyperpolarization may be performed using para-hydrogen induced polarization techniques. As appreciated, other temperature ranges and/or other hyperpolarization technique may be also used.

The solid state hyperpolarized compound is further adjusted for administration into a subject. In some embodiments, the method comprising prior to administration, a step of dissolving the solid state hyperpolarized compound in an aqueous solution to obtain the hyperpolarized compound in solution. In some embodiments, the aqueous solution comprising $D_2O$.

In another aspect the invention provides a method for diagnosing a condition or disease in a subject, said method comprising:

hyperpolarizing a compound comprising at least one isotopically labeled nitrogen atom to obtain a hyperpolarized compound in solid state;
dissolution of the hyperpolarized compound in solid state in an aqueous solution to obtain a solubilized compound;
administrating to the subject an effective amount of the solubilized hyperpolarized compound;
monitoring the hyperpolarized compound,
thereby diagnosing the condition or disease in the subject.

As described herein, monitoring and detection a signal from the compounds for the invention may be performed by any non-invasive or invasive method, preferably, as detailed herein, by MRS, MRI, magnetic resonance spectroscopic imaging, and PET.

In the context of the present disclosure, when referring to diagnosis and specifically to MRS and/or MRI diagnosis it should be understood to encompass a medical imaging technique used in radiology to provide spectra or to form pictures (images) of the anatomy and the physiological processes of the body in both health and disease.

MRS and MRI diagnosis makes use of magnetic fields, radio waves, and in case of MRI also field gradients to generate at least one spectrum or at least one image of the organs in the body.

In some embodiments, the monitoring is performed by means of MRS and/or MRI using a magnetic resonance scanner (an MRI scanner). Magnetic resonance signals obtained may be converted by conventional manipulations into 2-, 3- or 4-dimensional data (spatial and temporal) including metabolic, kinetic, diffusion, relaxation, and physiological data. The magnetic resonance spectroscopy may be conducted by any suitable probe, for example using a $^1H$ RF coil, $^{15}N$ RF coil, a D RF coil or a double tuned RF coil ($^{15}N/D$ or $^{15}N/H$).

In some embodiments, the monitoring is by acquiring $^1H$, $^2H$ and/or $^{15}N$ magnetic resonance (MR) spectrum and/or image from a tissue in the subject (MRS and/or MRI).

In some embodiments, the monitoring is by acquiring at least one $^1H$ spectrum. In some other embodiments, the monitoring is by acquiring at least one $^{15}N$ spectrum. In some further embodiments, the monitoring is by acquiring at least one $^1H$ image. In some other embodiments, the monitoring is by acquiring at least one $^{15}N$ image.

Detecting such signal using MR can be done by using for example specialized probes for acquiring the signal. For example, diagnosis of breast cancer may be done by subjecting a subject to magnetic field and using specific MR sequences and equipment (e.g. probes) to acquire signal from the breast region of a subject.

In some embodiments, the methods of the invention comprises a step of detecting a signal prior to administration of the compound. This may be possible by exposing the subject to magnetic field using MR to obtain a detectable signal. In some embodiments, prior to administration of the compounds of the invention, at least one anatomical $^1H$ image may be acquired.

In some embodiments, prior to administration of the compounds of the invention, suspected regions of having a disease or condition may be recorded using similar conditions to the conditions at which the compound is acquired to obtain base-line information.

In some embodiments, the method comprising prior to the administration step, acquiring at least one $^1H$, $^2H$ or $^{15}N$ MR spectrum and/or image from the subject's body or any one or more regions thereof. Monitoring the subject or any subject's region may be subjected to signal analysis of the MR spectrum or spectra and/or image processing of the acquired image(s). The results of the spectrum and/or image is indicative for the methods described herein.

In some embodiments, the method comprising comparing at least one parameter obtained from the at least one $^1H$, $^2H$ or $^{15}N$ MR spectrum and/or image to at least one parameter obtained from the at least one $^1H$, $^2H$ or $^{15}N$ MR spectrum and/or image in the same subject at an earlier point in time, wherein the comparison permits diagnosis of the disease.

In some embodiments, the method comprising comparing at least one parameter obtained spectrum and/or image analysis to at least one parameter obtained from spectrum and/or image analysis in the same subject obtained at an earlier point in time, wherein the comparison permits diagnosis of the disease. The earlier time point may be for example, prior to compound administration.

The compound described herein comprising at least one labeled nitrogen atom and being in a hyperpolarized state may be denoted as MR contrast agent. The term "contrast agent" refers to a substance used to increase the visual perception of structures or fluids within the body in medical imaging. In some embodiments, the labeled hyperpolarized compound is for use in diagnosis of a condition or a disease in a subject. The diagnosis is possible due to the fact that the compound described herein have the ability to differentiate between anatomical structures/fluids within tissue. In some embodiments, the contrast agent is [$^{15}N$]nitrate, preferably a salt of [$^{15}N$]nitrate, at times Na[$^{15}N$]nitrate. In some other embodiments, the contrast agent is [$^{15}N$]urea, [$^{15}N_2$]urea, [$^{15}ND$]urea, [$^{15}ND_2$], [$^{15}ND_3$], [$^{15}ND_4$], [$^{15}N_2D$], [$^{15}N_2D_2$], [$^{15}N_2D_3$], [$^{15}N_2D_4$] or any combination thereof.

In some embodiments, the diagnostic methods comprises administration of hyperpolarized [$^{15}N$]nitrate, preferably Na[$^{15}N$]nitrate in a solution form. In some other embodiments, the diagnostic methods comprises administration of hyperpolarized [$^{15}N$]urea, [$^{15}N_2$]urea, [$^{15}ND$]urea, [$^{15}ND_2$], [$^{15}ND_3$], [$^{15}ND_4$], [$^{15}N_2D$], [$^{15}N_2D_2$], [$^{15}N_2D_3$], [$^{15}N_2D_4$] or any combination thereof in a solution form.

In some embodiments, the compound according to the invention is the only (or main) contrast agent used. In other embodiments, it is used in combination with another contrast agent.

As detailed herein, the ability of the compounds of the invention to be used as contrast agents mainly depend on their relaxation time ($T_1$). As also noted above, the effective lifetime of the compound described herein, determines the time period at which the spin polarization is maintained and hence the time period at which the compound carries the increased signal can be detected by MR. Thus, in order to maximize the effectiveness of the compound, the compound should be administered to the subject at a time period of between 10 seconds to 240 seconds after dissolving the compound in the aqueous solution, at times between 20 seconds to 200 seconds, at times between 50 seconds to 100 seconds. In some embodiments, the subject is administered with consecutive doses of the hyperpolarized compound.

The compound, compositions or kits used according to the invention may be utilized for imaging a region or organ of a subject's body after or during treatment or otherwise state of a disease, it may be further utilized in determining severity of the disease, for, e.g., enabling determination of treatment effectiveness and continued treatment. Therefore, the compound, compositions or kits may be further utilized in a method for monitoring a disease state in a subject. In such a method, the subject is administered with the compound, the subject's body or any one or more regions thereof is imaged, to obtain at least one imaging parameter indicative of the disease or disorder state, and comparing said at least one imaging parameter to at least one parameter obtained from said subject at an earlier point in time or upon identification of, e.g., at least one symptom associated with said disease or disorder, wherein the comparison permits determining the progression of the disease or disorder state.

Effective monitoring, made possible by utilization of a compound of the invention, involves obtaining multiple parameters indicative of a disease state and progression at various points in time, prior to, during or after commencement of treatment, and comparing the collected data to determine any one therapeutic parameter. The monitoring may be conducted over a period of time, for example every few days or weeks, once a week, once a month, at the onset of treatment and at any time thereafter, etc.

In a further aspect, the invention provides a method for determining the severity of a disease or disorder in a subject, the method comprising administering to said subject a compound according to the invention, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the severity of the disease or disorder in the subject.

In another aspect the invention provides a method for determining the effectiveness of a therapeutic treatment of a disease or disorder in a subject, the method comprising administering to said subject a compound according to the invention, imaging the subject's body or region thereof to obtain at least one imaging parameter (e.g., indicative of the state of the disease or disorder), and comparing said at least one imaging parameter to at least one parameter obtained from said subject at the onset of treatment or prior to treatment commencement, wherein the comparison permits determining the effectiveness of the therapeutic treatment of the disease or disorder in the subject.

The determination of the effectiveness of treatment may be achieved at the end of treatment or at any point in time during the treatment period. Generally, and depending on the disease and disease state, the effectiveness is indicated by any one or more changes in the disease state or any symptom associated therewith, such as decreased proliferation.

In some embodiments, the methods of the invention are used for evaluating the effectiveness of drug treatment in cancer treatment, for example, in evaluating the ability of a drug to reduce the size of a tumor or to prevent the tumor from growing, wherein the method comprises imaging the tumor with a compound according to the invention, as disclosed herein, and measuring the size of the tumor; administering the drug to the subject to affect at least one of reduction in the size of the tumor and prevention of growth of the tumor; re-imaging the tumor with the same or different compound and measuring the size of the tumor, and comparing the size of tumor after administration of the drug to the size of the tumor prior to administration of the drug. As compounds of the invention are not intended nor suitable for therapeutic use, the "drug" used for treatment is a material different from any compound used for diagnosis and accordance with the invention.

In a further aspect, the disclosure provides a compound being labeled glycerophosphocholine compound. In some embodiments, the compound being [$^{15}$N]glycerophosphocholine. In some further embodiments, the compound comprising at least one labeled hydrogen atom. In other embodiments, the compound being [$^{15}$N,D$_9$]glycerophosphocholine. As described herein, the compound [$^{15}$N,D$_9$]glycerophosphocholine may be in a hyperpolarized state.

The present disclosure also encompasses a composition and/or a kit comprising a labeled glycerophosphocholine compound. For example, a kit comprising a composition comprising [$^{15}$N,D$_9$]glycerophosphocholine and instructions for use thereof.

In another aspect, the disclosure provides a compound comprising at least one isotopically labeled nitrogen atom, wherein the compound is in a hyperpolarized state and wherein the compound is at least one of an amine, an amide, an imide, a nitrogen-containing ion or an amino acid.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

As used herein the term "about" refers to ±10%.

The term subject as used herein refers to human and non-human subjects.

NON-LIMITING EXAMPLES

Example 1—Hyperpolarization of N-15 Labeled Compounds

Structure of compound containing $^{15}$N sites bound to labile protons studied in this work are shown in the scheme 1 below. The nitrogen sites labeled with $^{15}$N are indicated and labile protons that are to be replaced by deuterons upon dissolution in D$_2$O are encircled.

Scheme 1

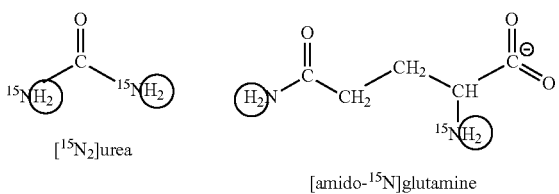

[$^{15}$N$_2$]urea

[amido-$^{15}$N]glutamine

-continued

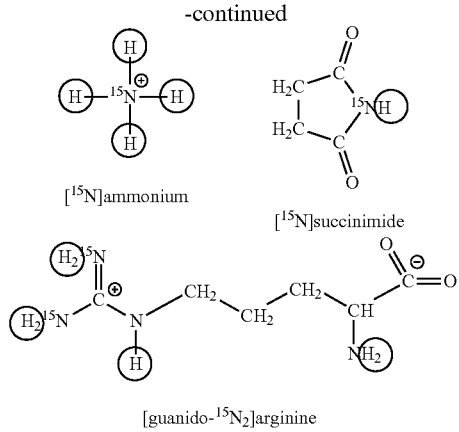

[$^{15}$N]ammonium

[$^{15}$N]succinimide

[guanido-$^{15}$N$_2$]arginine

The choline metabolite glycerophosphocholine (GPC) is Generally Regarded As Safe (GRAS), as noted in a 2012 letter to the FDA. The safe dose for an intravenous injection of GPC to mice and rats was 521 and 781 mg/kg, respectively. Dogs receiving a daily intravenous injection of up to 120 mg/kg of GPC for 28 days showed only mild and reversible mood changes and no mortality. The $T_1$ of [$^{15}$N, D$_9$]GPC was estimated to be of the same order of magnitude as that of [$^{15}$N,D$_9$]choline—about 6 min. In light of its promising $^{15}$N $T_1$ and its positive safety profile, one of the compounds described herein is of [$^{15}$N,D$_9$]GPC and it's hyperpolarized state.

FIG. 1 shows the $^{15}$N $T_1$s of compounds and formulations (compositions) in water and D$_2$O at 5.8T. As can be seen, the decay of the nitrate moiety for $^{15}$N hyperpolarization is not affected much by the protonation of the water. In the dissolution in physiological saline shown in FIG. 1, the T was 102 s, meaning that also the addition of osmotic pressure did not significantly affect the hyperpolarized decay. These advantages are expected also for [$^{15}$N, D$_9$]GPC. The value shown here for this compound is a speculation, based on previous results obtained with [D$_9$] choline.

Although non-protonated positions of $^{15}$N show advantages for $^{15}$N hyperpolarization, a strategy for improving the lifetime/visibility of protonated $^{15}$N positions was suggested for ammonium, urea, arginine, and succinimide.

Figure 2:
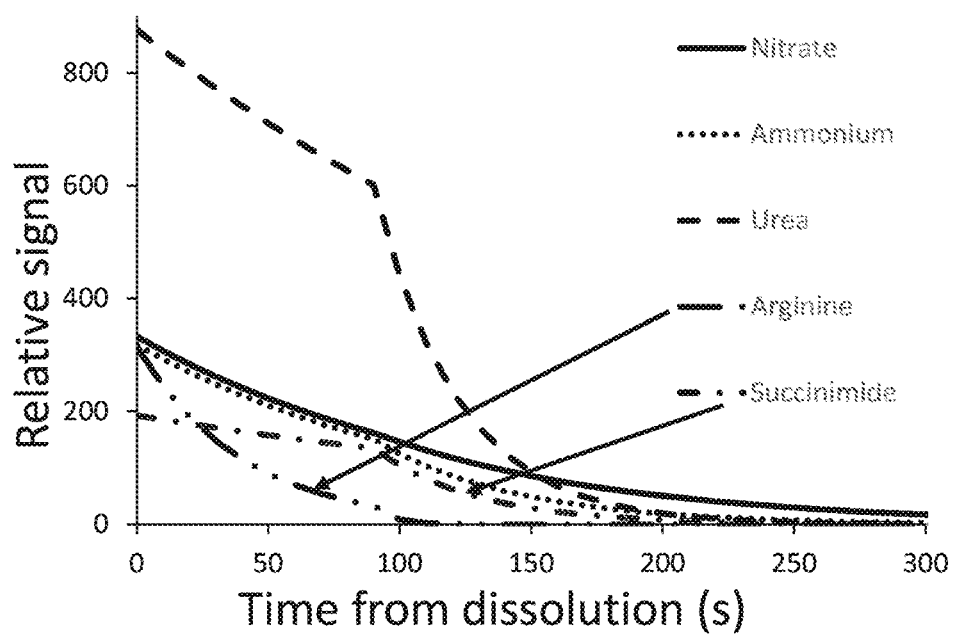
FIG. 2. Decay curves of $^{15}N$ signals, the $^{15}N$ signal was measured for 1.5 min in $D_2O$ (from the dDNP device to the subject) and then continuation of the decay in $H_2O$.

To provide an estimate for the relative signals of these hyperpolarized compounds in the body, and the potential effect of D$_2$O dissolution for protonated positions, hypothetical decay curves were plotted based on the T values presented in FIG. 2. The decay curves presented in FIG. 2 simulate the decay of the signal for 1.5 min in D$_2$O (from the dDNP device to the subject) and then continuation of the decay in H$_2$O—corresponding to the decay of the signal in the subject's body—under the assumption that the injected dose immediately mixes with the large content of water in the body. The starting level of the signal is calculated based on 100 mg of solid-state formulation, the solubility of the compound in the formulation (mole compound/mg formulation), and the number of $^{15}$N nuclei per molecule. This hypothetical relative signal behavior assumes an equal level of solid state polarization level for all compounds (per mole $^{15}$N) and that all compounds are injected at the same dose in terms of mole/kg body weight. The advantage of the nitrate (green line) is clear in terms of long term visibility and the relatively slow loss of polarization in both media. It appears that nitrate could serve as a candidate for a clinical MRI contrast agent. However, urea, ammonium, and succinimide also show prolonged overall visibility, despite the faster decay in water.

Example 2: Hyperpolarized [$^{15}$N] Nitrate as a Potential Long Lived Hyperpolarized Contrast Agent for MRI Nitrite (NO$_2$) is a bioactive ion in mammals and serves as a reservoir of the vasodilation agent nitric oxide (NO). However, nitrate (NO$_3$—) is considered relatively biologically inactive and was even used as a control in studies of the action of nitrite. The half-life of nitrate in the circulation is about 5-6 h while that of nitrite is 20 min. Since the discovery that nitrate reductase activity occurs also in mammalian tissues and not only in bacteria, much research into the nature and level of this activity ensued and beneficial effects of nitrates have been reported in the context of several diseases and conditions such as diabetes and heart failure.

Materials and Methods

Chemicals

Sodium [$^{15}$N]nitrate and sodium [$^{15}$N]nitrite were purchased from Sigma-Aldrich, Rehovot, Israel.

The OXO63 radical (GE Healthcare, UK) was obtained from Oxford Instruments Molecular Biotools (Oxford, UK). [$^{15}$N$_2$]urea was purchased from Cambridge Isotope Laboratories (Andover, Mass., USA).

Nitrate and Nitrite Formulations

To explore the hyperpolarized state of nitrate and the nitrite anions in solution the following formulations were prepared for solid-state polarization: for the nitrate anion, 85.2 mg of Na$^{15}$NO$_3$, 3.7 mg of OXO63 radical, 76 mg of glycerol, and 145 mg D$_2$O. For the nitrite anion, 59.5 mg of Na$^{15}$NO$_2$, 2.2 mg of OXO63 radical, and 129.65 mg of D$_2$O:[$^{13}$C$_3$]glycerol 7:3 mixture. Carbon-13 labeled glycerol was used to monitor the presence of the sample in the polarization chamber.

For the samples that were not prepared with [$^{13}$C$_3$] glycerol, a small amount of [$^{13}$C,D$_7$]glucose (up to 13.3 mg) or [1-$^{13}$C]pyruvic acid (up to 1.8 mg) formulation was added as a dot on the cup wall-to indicate, using the polarizer $^{13}$C spectrometer, that the sample is in the polarization chamber.

A vitrification assay showed that these formulations indeed formed a glass upon rapid freezing to cryogenic temperature (liquid nitrogen).

DNP Spin Polarization and Dissolution

Spin polarization and fast dissolution were carried out in a dDNP set-up (HyperSense, Oxford Instruments Molecular Biotools, Oxford, UK). As detailed below, a microwave frequency of 94.100 GHz was determined as optimal.

The dissolution process is detailed in the results section. Briefly: 20-90 mg of the sodium [$^{15}$N]nitrate formulation were placed in a polarization sample cup, polarized by microwave irradiation, and then quickly dissolved in 4 mL of superheated aqueous media (170° C. and 10 bar). Unless otherwise stated, the dissolved hyperpolarized solution was directly injected to a screw cup 10 mm NMR tube in a 5.8T NMR spectrometer via a PTFE line of about 2.4 m length with 3 s of He(g) chase. This line was wrapped with a heating tape (MRC, Holon, Israel) that enabled control over the temperature of the dissolution medium arriving to the NMR tube directly or to a collection tube in the fringe field of the spectrometer. $^{15}$N-Nuclear Magnetic Resonance (NMR) spectra were continuously recorded immediately at the start of the dissolution process. The hyperpolarized signals appeared in the spectra at about 10-14 s from the start of the dissolution process (meaning that the dissolution process and the chase of the media into the NMR tube occurred within about 10-14 s). In the experiments in body fluids and in experiments in which the hyperpolarized solution was first cooled to temperatures below room temperature, the dissolution media was first collected in a conical tube placed in the spectrometer's fringe field, and then was injected by syringe via a PEEK line to the NMR tube that was placed in the magnet.

Modification of the Hyperpolarized Solution Temperature Prior to Arrival to the Spectrometer The temperature of the solution leaving the dDNP device was not lower than 26° C. For heating this hyperpolarized solution prior to arrival to the NMR tube, the PTFE line leading the hyperpolarized solution out of the spin polarization device was wrapped with a heating tape connected to a temperature controller (MRC, Holon, Israel). In this way, hyperpolarized solutions at temperatures higher than 26° C. could be obtained. For cooling the hyperpolarized solution, the heating tape was not turned on and the dissolution medium was mixed with 0 to 4 mL of $D_2O$ at 2° C. in a collection tube placed in ice-water bath in the fringe field of the magnet, prior to injection.

$^{15}$N-NMR $^{15}$N-NMR spectroscopy was performed in a 5.8T NMR spectrometer (RS2D, Mundolsheim, France), using a 10 mm broad-band NMR probe. The chemical shift scale of the spectra presented herein was calibrated based on a separate measurement of a $[^{15}N_2]$urea standard sample (4M in $H_2O$: $D_2O$ 80:20), carried out prior to hyperpolarized $^{15}$N acquisitions, calibrating the $[^{15}N_2]$urea signal to −306 ppm (relative to nitromethane). For enhancement factor calculation, the spectra were collected with a high flip angle of 300 and a repetition time of 2 s. For $T_1$ calculation, the spectra were acquired with a low flip angle of 100 and a longer repetition time of 5-10 s.

Online Temperature Sensing in the NMR Spectrometer

The temperature in the NMR tube was continuously monitored using an NMR compatible temperature probe (Osensa, Burnaby, BC, Canada). A typical example of such a measurement is shown below in the results section under the header "Monitoring of sample temperature during the NMR measurements and simultaneous $T_1$ Determinations").

Processing and Data Analysis

Spectral processing was performed using MNova (Mestrelab Research, Santiago de Compostela, Spain).

Determination of the $T_1$ of the hyperpolarized sites was performed by curve fitting of the signal decay to the following equation: $S(t)=S_0 \cdot e^{-t/T_1} \cdot (\cos \theta)^{t/TR}$, in which TR, the time between excitations, and $\theta$, the nutation angle of excitation, are known. Curve fitting was performed using Matlab (Mathworks, Natick, Mass., USA).

The absolute enhancement factor was determined by comparing the maximal SNR of the magnitude signal multiplied by the linewidth at half-height obtained under hyperpolarized conditions to the intensity of the thermal equilibrium signal of the same sample (analyzed in the same way). The spectrum at thermal equilibrium was acquired with the same nutation angle under fully relaxed conditions. The same spectral acquisition parameters (spectral width, number of points, receiver gain) and processing parameters (apodization, zero-filling) were used in the analysis of both spectra and the thermal equilibrium signal was corrected for the number of scans.

Figure 3A:
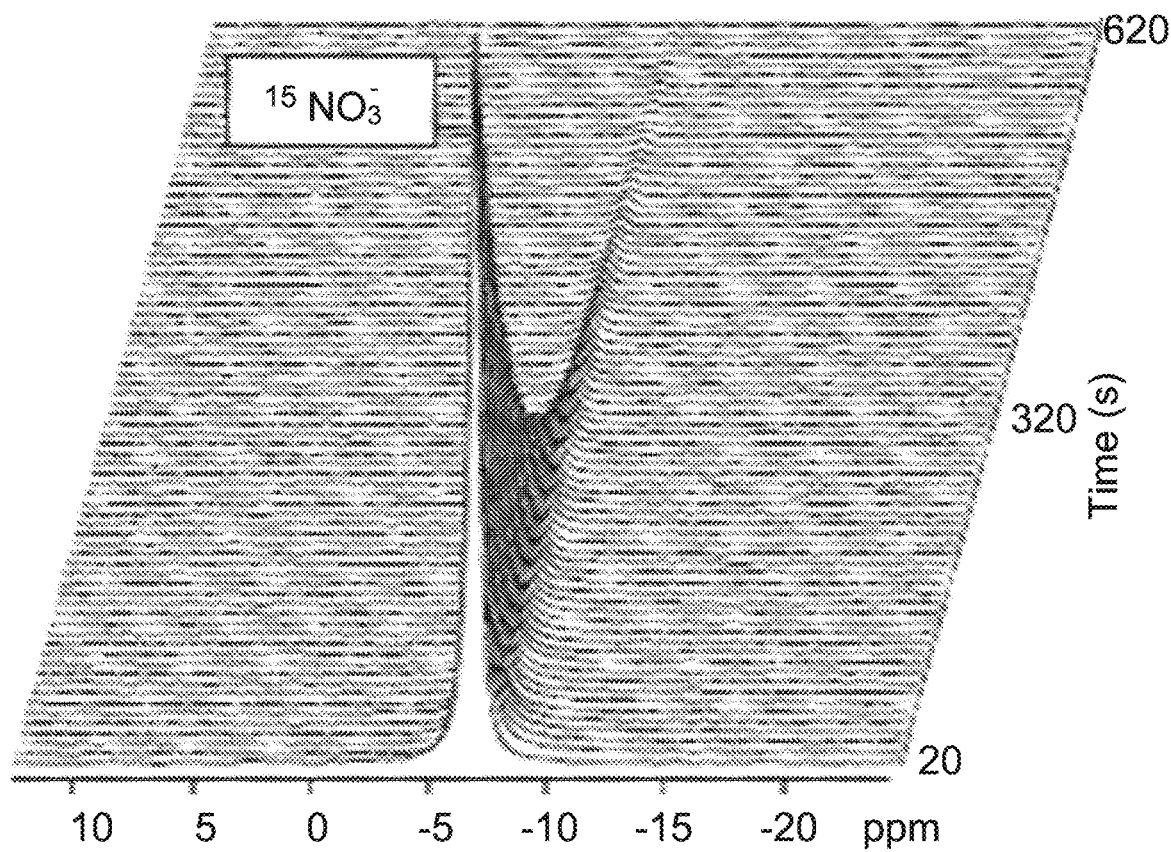
FIGS. 3A-3D Observation of hyperpolarized [$^{15}N$]nitrate and the effects of solvent protonation and salinity on its $T_1$, FIG. 3A Stacked $^{15}N$ spectra of hyperpolarized sodium [$^{15}N$]nitrate in $D_2O$; the spectra were recorded with a flip angle of 100 and a repetition time of 8 s, with a time frame of 20-620 s from the onset of the dissolution process is shown.
Figure 3B:
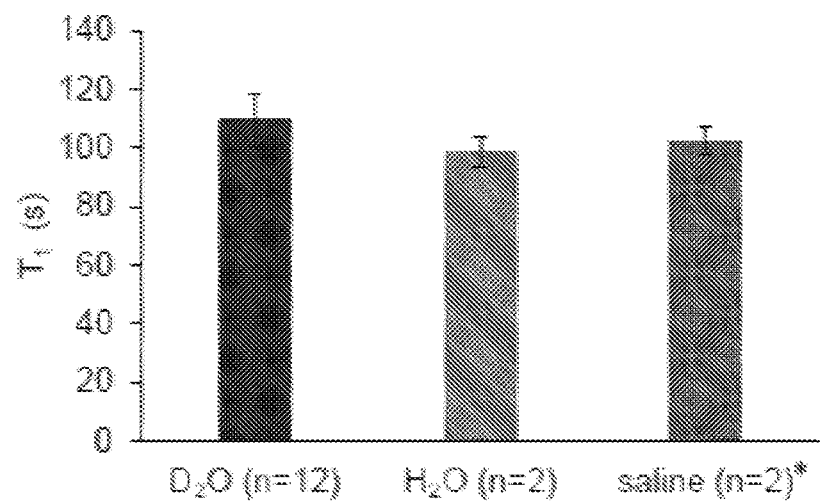

Results $[^{15}N]$Nitrate is Observed in a Hyperpolarized State and its Decay is Independent of Water Protonation or Salinity Applying the dDNP technology to formulations of $[^{15}N]$ nitrate with the trityl radical we could observe the hyperpolarized state of $[^{15}N]$nitrate at 5.8 T, for about 10 min (FIG. 3A). The maximal enhancement factor, calculated for the 1 signal in solution, was 5,298. As shown below, when extrapolated to the case of a common clinical MRI magnetic field of 1.5T this enhancement factor converts to about 20,500. This enhancement factor was obtained following 2.5 h of polarization at 1.5-1.6 K. This enhancement factor corresponds to 1% $^{15}$N polarization. Other enhancement factors that were found on varied experimental conditions are summarized in the below under the header "Enhancement factors of hyperpolarized $[^{15}N]$nitrate on selected individual experiments". The $T_1$ of the $^{15}$N site in $[^{15}N]$ nitrate was long-reaching 109±9 s (n=12) in $D_2O$ at a temperature range of 34-44° C. (FIG. 3B). FIG. 3B shows $T_1$ values of hyperpolarized $[^{15}N]$nitrate in solution, at concentrations of 19-29 mM sodium $[^{15}N]$nitrate, $T_1$s were determined in $D_2O$, $H_2O$, and medical grade physiological saline (154 mM NaCl in $H_2O$), at a temperature range of 34-44° C.,*denotes one sample was dissolved in of 4 mL saline solution and another sample was dissolved in 4 mL of saline which were then mixed with 1 mL human saliva (experiment to be described above).

For several hyperpolarized compounds, dissolution in $D_2O$ has been shown to prolong the $T_1$ time significantly. Here, it was found that the $[^{15}N]$nitrate $T_1$ was not significantly affected by the water protonation (FIG. 3B) with the $T_1$ in water reaching 98±5 s (n=2). For biological applications, it is necessary to investigate the $T_1$ in solutions isosmotic to blood plasma (physiological saline, ~300 mOsm), such that they can be safely injected. In general, it has been shown that in such saline solutions the hyperpolarized site's $T_1$ is shortened. Surprisingly, dissolution of hyperpolarized $[^{15}N]$nitrate in physiological saline did not significantly reduce its $T_1$, which was found to be 102±5 s (n=2) (FIG. 3B). These findings suggested that the $T_1$ relaxation of $[^{15}N]$nitrate is relatively immune to changes in the basic physicochemical properties of the lattice, and therefore are encouraging with regards to the potential use of $[^{15}N]$nitrate as a long-lived contrast agent for MRI.

Figure 3C:
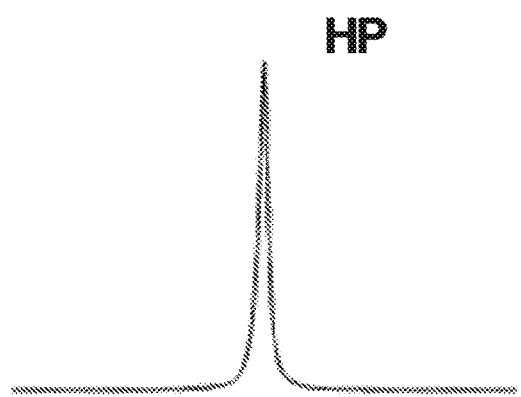
Figure 3D:
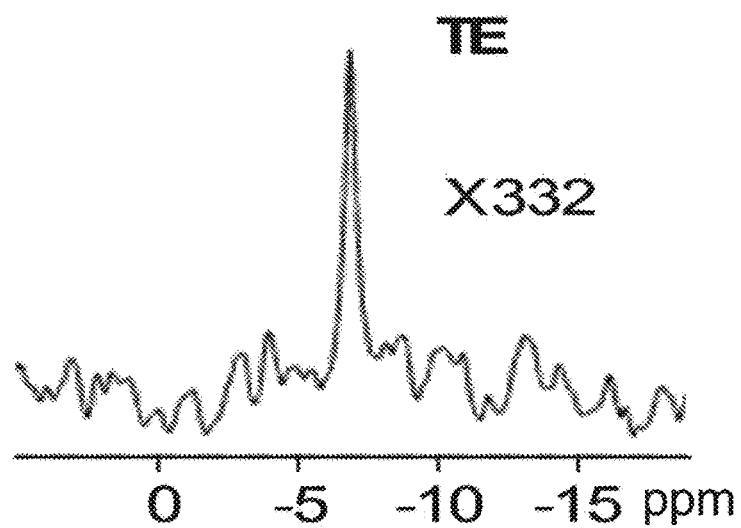

The $^{15}$N-NMR spectra of hyperpolarized $^{15}$N in sodium nitrate (Na$^{15}$NO$_3$) dissolved in physiological saline is shown in FIG. 3C. A 10 nutation angle pulse was applied every 8 s, at a field of 5.8 T, at a temperature of 38° C. The $^{15}$NO$_3^-$ signal is visible for about 8 min. FIGS. 3C and 3D show a comparison of the hyperpolarized signal (HP) of $^{15}$N-nitrate to the signal of the same sample at thermal equilibrium (TE). The nutation angle for both spectra was 30°. The HP spectrum was acquired with a single scan and the TE spectrum was acquired with 64 scans over 10 h and 40 min. All of the spectra were processed with a line broadening of 10 Hz. From this experiment it was found that the percent polarization of the $^{15}$N was only 0.6%.

Enhancement Factors of Hyperpolarized $[^{15}N]$Nitrate on Selected Individual Experiments in the same spectrometer used to record the hyperpolarized signal (5.8T), as described in the Methods section, and then projected to the expected enhancement factors at a common clinical scanner at 1.5T. Enhancement factors were calculated with reference to a spectrum of the same sample. The maximal value of the enhancement factor is shown in Table 1 below (Experiment No. 19 in Table 1).

TABLE 1

A summary of the enhancement factors determined on
multiple individual hyperpolarized [$^{15}$N] nitrate experiments.

| Exp. No. | Solvent for dissolution | Frequency of irradiation (GHz) | Polarization Time (min) | Temperature range (° C.) | Enhancement Factor relative to the same sample at thermal equilibrium at 5.8T | Projected enhancement factor relative to thermal signal at 1.5T |
|---|---|---|---|---|---|---|
| 1 | D$_2$O | 94.116 | 256 | 38.5-43 | 4,024 | 15,559 |
| 2 | D$_2$O | 94.116 | 164 | 36.5-44 | 4,709 | 18,208 |
| 3 | H$_2$O | 94.116 | 157 | 36.6-39 | 4,281 | 16,553 |
| 4 | Saline + 10% D$_2$O | 94.116 | 150 | 36.6-41.4 | 3,080 | 11,909 |
| 5 | D$_2$O | 94.116 | 60 | 37-39.2 | 2,339 | 9,044 |
| 6 | D$_2$O | 94.116 | 30 | 37.2-41.4 | 1,824 | 7,053 |
| 7 | D$_2$O | 94.116 | 105 | 36-40.2 | 2,709 | 10,475 |
| 8 | D$_2$O | 94.110 | 30 | 38-42 | 2,162 | 8,360 |
| 9 | D$_2$O | 94.122 | 30 | 35.5-39 | 1,647 | 6,368 |
| 10 | D$_2$O | 94.092 | 30 | 36.4-40.4 | 3,180 | 12,296 |
| 11 | D$_2$O | 94.104 | 30 | 36-41.5 | 3,228 | 12,482 |
| 12 | D$_2$O | 94.098 | 30 | 39.3-42.5 | 2,965 | 11,465 |
| 13 | D$_2$O | 94.128 | 30 | 38.6-41.5 | 1,436 | 5,553 |
| 14 | D$_2$O | 94.134 | 30 | 38.8-41 | 756 | 2,923 |
| 15 | D$_2$O | 94.086 | 30 | 38.1-39.6 | 3,894 | 15,057 |
| 16 | D$_2$O | 94.146 | 30 | 39-42.6 | 1,166 | 4,509 |
| 17 | D$_2$O | 94.080 | 30 | not recorded | 3,778 | 14,608 |
| 18 | D$_2$O | 94.152 | 30 | 39.6-49.8 | 1,615 | 6,245 |
| 19 | H$_2$O | 94.100 | 150 | 34.3-40.4 | 5,298 | 20,486 |

Hyperpolarized [$^{15}$N]Nirate is not Significantly Metabolized in Body Fluids

In order to predict the stability of hyperpolarized [$^{15}$N] nitrate in vivo, the $^{15}$N signal was monitored upon dissolution of hyperpolarized [$^{15}$N]nitrate in human blood and saliva. In order to monitor the potential conversion of [$^{15}$N]nitrate to [$^{15}$N]nitrite in these fluids, it was first aimed at characterizing the hyperpolarized signal of [$^{15}$N]nitrite. The results are summarized in FIG. 4.

Figure 4A:
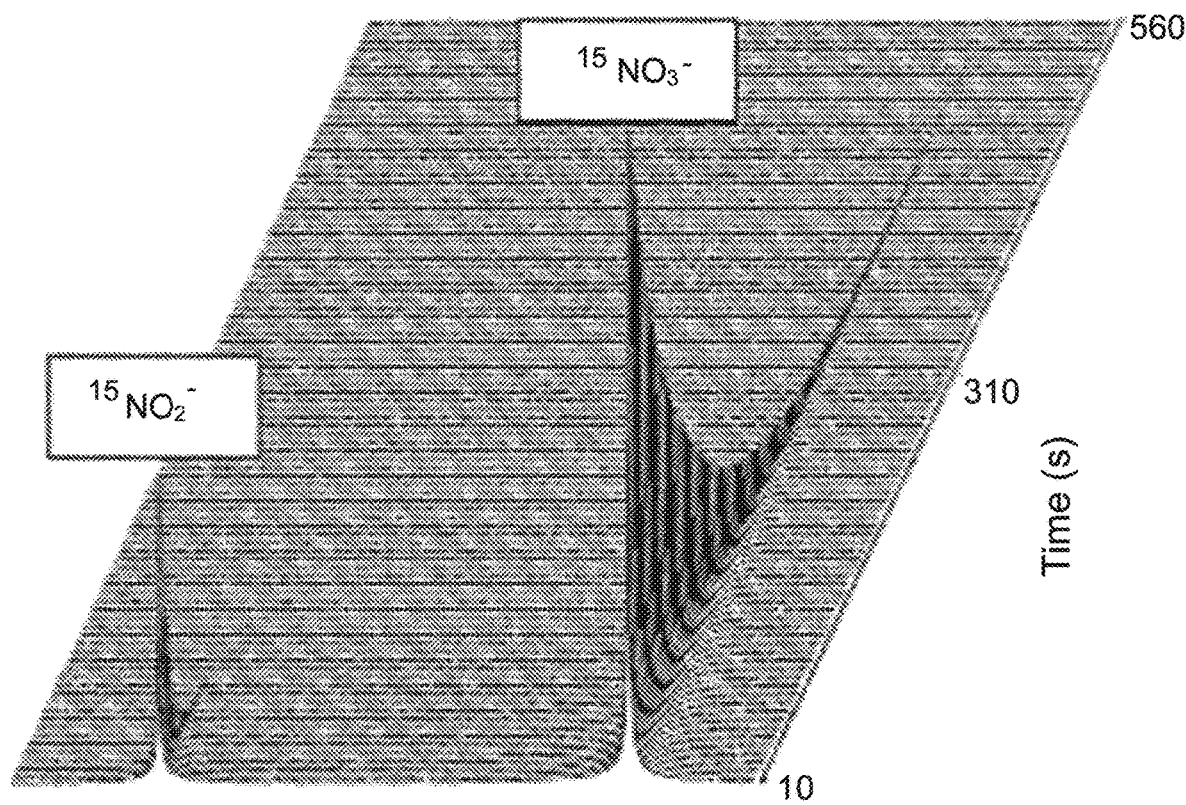

All the spectra in FIG. 4 are presented with an exponential multiplication of 10 Hz, and the line widths of the signals prior to the exponential multiplication were as follows: in FIG. 4A and FIG. 4B the [$^{15}$N]nitrate signal 3.2 Hz and the [$^{15}$N]nitrite signal 3.6 Hz; in FIG. 4C 1.1 Hz; in FIG. 4D 4.4 Hz; in FIG. 4E 4.3 Hz, in FIG. 4F 2.1 Hz; and in FIG. 4G 1.6 Hz.

FIG. 4A shows $^{15}$N spectra of co-polarized sodium [$^{15}$N] nitrate and sodium [$^{15}$N]nitrite in D$_2$O (29 mM and 47 mM, respectively), at 37-42° C., the signals of [$^{15}$N]nitrate and [$^{15}$N]nitrite appear at −6.8 and 226.2 ppm, respectively. [$^{15}$N]nitrite was polarized and visualized in a hyperpolarized state (FIG. 4D). The $^{15}$N chemical shift of the [$^{15}$N]nitrite was 226.2 ppm (FIG. 4D), and its T$_1$ was found to be 14.8±0.6 s (n=2) and 13.6±0.5 s (n=2) in D$_2$O and in H$_2$O, respectively. The effect of this shorter T$_1$ of [$^{15}$N]nitrite compared to [$^{15}$N]nitrate can be observed in the co-polarization and simultaneous decay experiment shown in FIG. 4A, which demonstrates the smaller and faster decaying signal of hyperpolarized [$^{15}$N]nitrite, although its concentration was 1.6 fold higher. While the signal of the [$^{15}$N] nitrate can be observed for more than 500 s, the [$^{15}$N]nitrite signal is observed for only 55 s (FIG. 4A).

FIG. 4B shows a summation of the spectra shown in FIG. 4A, in which both of the signals were observed (a total of 15 spectra with repetition time of 5 s, recorded with a flip angle of 10°).

FIG. 4D shows a summation of the spectra recorded from a hyperpolarized sample of sodium [$^{15}$N]nitrite in D$_2$O (37 mM), at 38-41° C. (a total of 15 spectra with a repetition time of 5 s, recorded with a flip angle of 10°), a small hyperpolarized nitrate signal is observed which may be the result of conversion of [$^{15}$N]nitrous acid in water to [$^{15}$N] nitrate or an [$^{15}$N]nitrate impurity coming from the original material.

Although the T$_1$ of [$^{15}$N]nitrite is much shorter, it is sufficiently long that significant conversion of [$^{15}$N]nitrate to [$^{15}$N]nitrite should be observable during the hyperpolarized acquisition window. In the next step, the inventors wanted to examine the stability of [$^{15}$N]nitrate in blood—i.e. have searched for signs of conversion to [$^{15}$N]nitrite. To this end, hyperpolarized [$^{15}$N]nitrate was dissolved in 4 mL of medical grade saline and quickly injected to an NMR tube containing 10 mL of whole human blood (healthy volunteer), to form a homogenous mixture, and the hyperpolarized signal was monitored for 4 min at 32-36° C. and showed a T$_1$ of 29±1 s (the error represents the 95% confidence interval for the individual fit). The final concentration of the [$^{15}$N]nitrate in this saline/blood mixture was 25 mM. Throughout this time, only the [$^{15}$N]nitrate signal was detected.

Also, when combining all of the spectra that showed a signal, still the nitrate signal was the only signal that could be detected (FIG. 4E). This result suggests that the nitrate stability was not affected by the contact with the blood components.

Although the intended route of administration for hyperpolarized [$^{15}$N]nitrate is intravenous, the entero-salivary circulation recycles nitrate from the blood to the saliva, where it can be bacterially converted to [$^{15}$N]nitrite. For this reason it was important to determine also the potential conversion to hyperpolarized [$^{15}$N]nitrite in human saliva. To this end, hyperpolarized [$^{15}$N]nitrate was dissolved in 4 mL of medical grade saline and quickly injected to an NMR tube containing 1 mL of human saliva from a healthy volunteer (not using anti-bacterial mouth wash). The [$^{15}$N] nitrate hyperpolarized signal was monitored for more than 400 s at a temperature range of 37–42° C.

Throughout this time, only the [$^{15}$N]nitrate signal was observed and a hyperpolarized [$^{15}$N]nitrite signal was not observed (FIG. 4F). To test for the presence of [$^{15}$N]nitrite in this saline-saliva sample after the hyperpolarized state had decayed, the same sample was scanned at thermal equilibrium as well. The sample was scanned for 20 h, at room temperature. The summed spectrum, (12,000 averages acquired with a repetition time of 6 s and a flip angle of 10°), shows the [$^{15}$N]nitrate signal only (FIG. 4G). FIG. 4G shows a summation of thermal equilibrium spectra of sodium [$^{15}$N]nitrate (18 mM) in a saliva and saline mixture (same sample as in FIG. 4F), recorded at room temperature for 20 h, (a total of 12,000 averages with repetition time of 6 s) with a flip angle of 10°.

These results suggest that [$^{15}$N]nitrate was not significantly metabolized in blood or in saliva of the individual volunteer. Further tests with human saliva, conducted for longer measurement times, are described in the following section.

Long Term Monitoring of the Conversion of [$^{15}$N]Nitrate to [$^{15}$N]Nitrite in Solutions Containing Human Saliva The same sample of sodium [$^{15}$N]nitrate in the saline-saliva solution presented in FIG. 4G (which did not show metabolism) was scanned about a month later and showed about equal signals of [$^{15}$N]nitrate and [$^{15}$N]nitrite. To investigate the stability of the [$^{15}$N]nitrate in saline and saline saliva-solutions using controlled conditions, this experiment was repeated in the following way.

First the stability of [$^{15}$N]nitrate in the saline solution was investigated. In order to mimic the experiment with hyperpolarized [$^{15}$N]nitrate in terms of the DNP formulation and the dissolution components, 9.97 mg of [$^{15}$N]nitrate and 2.60 mg of glucose were dissolved in 26.15 mg of a $D_2O$:glycerol mixture (66:34). Then, 4.59 mL saline and 0.66 mL of $D_2O$ were added to this mixture. This solution was transferred to an NMR tube and scanned for 5 days. $^{15}$N fully-relaxed spectra were recorded in blocks of about 4 h, whereas each block consisted of 720 averages with a 30 flip angle and a repetition time of 20 s. The summation of this 5 days scan is shown in FIG. 5A. Only the [$^{15}$N]nitrate signal appears in the spectrum, suggesting that [$^{15}$N]nitrate is stable at room temperature in this solution for this period time.

In the next step, this solution was divided into 2 samples, in the following manner: 3 mL of this solution were combined with 0.75 mL of human saliva and the combined solution was scanned for 5 days. The rest of the solution (without human saliva) was kept outside the magnet at room temperature. The resulting spectrum of the [$^{15}$N]nitrate in the saline-saliva solution. FIG. 5B shows the signal of [$^{15}$N]nitrite in addition to [$^{15}$N]nitrate, suggesting conversion due to the bacteria in the saliva. FIG. 5C shows the resulting spectrum of an additional 5 days scan of the [$^{15}$N]nitrate in saline solution without human saliva. Despite the longer duration of presence of [$^{15}$N]nitrate in saline, exposed to environmental bacteria, no conversion to [$^{15}$N] nitrite was observed. These results suggest that [$^{15}$N]nitrate in saline solution is stable at room temperature for at least 19 days (10 days of actual measurements and 9 days in between measurements). In addition, it suggests that the conversion to [$^{15}$N]nitrite was indeed catalyzed by human saliva microbiome. The conversion rate appeared to be about 23% in 5 days in a solution with a starting [$^{15}$N]nitrate concentration of 22 mM. Assuming a linear conversion rate of nitrate to nitrite, the conversion rate appears to be about 3.8 mole per day per 0.75 mL of saliva.

Hyperpolarized [$^{15}$N]Nitrate Shows Prolonged $T_1$ in Colder Solutions

For the duration required for transfer of the hyperpolarized solution from the polarizer to the subject, prior to intravenous administration, the temperature for holding of the solution is not limited to body temperature. It was hypothesized that for this transfer time, it may be beneficial to store the hyperpolarized solution at a colder temperature. To test this hypothesis, an experimental system was designed in which the hyperpolarized [$^{15}$N]nitrate solution is either 1) heated and directly injected to the spectrometer or 2) cooled down (with online temperature monitoring), and then injected to a nuclear magnetic resonance (NMR) tube in the spectrometer where the temperature is continuously monitored as well, and the $T_1$ decay is determined in parallel. Hyperpolarized decays in temperatures at a range of 10-50° C. were monitored in this way (FIG. 6). At a range of temperatures close to the human body temperature, 34-44° C., the $T_1$ was found to be 109±9 s (n=12), and at 40-50° C. the $T_1$ was similar at 105 s (n=1). Despite many attempts to analyze segments of the decay data and resolve better a possible dependence of the decay rate on temperature, we could not detect any such dependence and we concluded that in the temperature range of 34-50° C., the $T_1$ of [$^{15}$N]nitrate does not change. However, at temperatures of 20-23° C. the $T_1$ was prolonged, reaching 139±6 s (n=2), and at 10-19° C. the $T_1$ was found to be 172±6 s (n=4). These findings support the hypothesis that in order to preserve the hyperpolarized state of [$^{15}$N]nitrate it is advantageous to quickly cool the hyperpolarized solution.

Figure 7A:
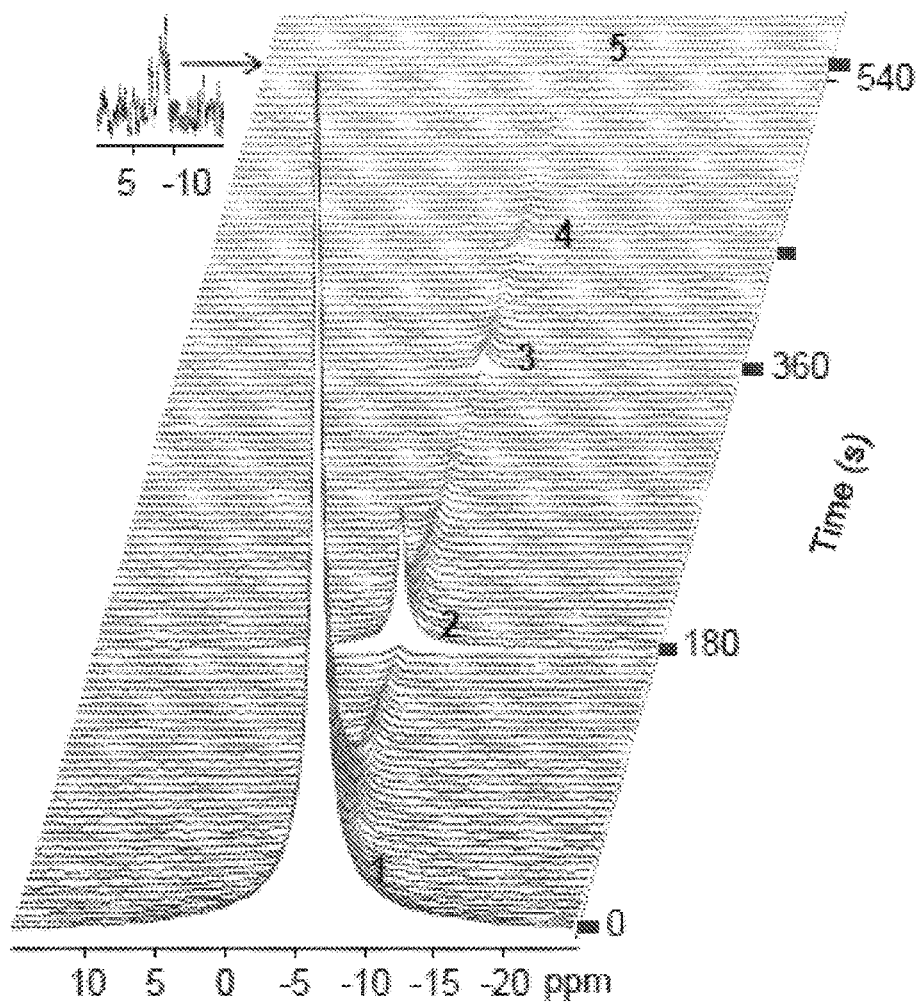
FIGS. 7A-7C Multiple hyperpolarized [$^{15}$N]nitrate injections to blood from a single hyperpolarized [$^{15}$N]nitrate dose, FIG. 7A $^{15}$N spectra of the consecutively injected hyperpolarized [$^{15}$N]nitrate in whole blood, spectra were acquired with a repetition time of 5 s and a flip angle of 10°, the red marks on the time axis show the injection times (0, 180, 360, 435 and 550 s).

Storage of Hyperpolarized [$^{15}$N]Nitrate in Cold Solution Enables Prolonged Use for Injection This prolonged $T_1$ of [$^{15}$N]nitrate in colder solutions can be capitalized on when observing hyperpolarized [$^{15}$N] nitrate signal in vivo, in particular when multiple perfusion measurements are desired, such that the hyperpolarized solution must be stored for long time periods before injection. To test the utility of cold storage of the hyperpolarized solution for repeated injections, FIG. 7 demonstrates the visibility of this signal in blood for up to 9 min, while in a previous injection to blood the signal was observed for only 4 min (FIG. 4E, decay not shown).

FIG. 7 shows a solution of 32.6 mM hyperpolarized sodium [$^{15}$N]nitrate in saline that was kept in an ice-water bath and ca. 1 mL volumes were injected to heparinized whole human blood in an NMR tube (4.5 mL). The injected volumes ranged in temperature from 16.4 to 1.7° C. The corresponding temperature range in the blood sample was 36.4-28.4° C.

To achieve this dramatic prolongation, the hyperpolarized [$^{15}$N]nitrate solution was injected to a collection tube placed in an ice-water bath in the fringe field of the magnet and containing 1 mL of ice-cold saline at (2° C.). The hyperpolarized solution reaches the collection tube at a minimum of 26-27° C. and cools down throughout the duration of the experiment. Small amounts of this cold hyperpolarized [$^{15}$N]nitrate solution (about 1 mL) were then injected into a blood sample already placed in the NMR spectrometer and maintained at 36° C. The small amounts of hyperpolarized solution were added to the blood sample at 0, 3, 6, 7.25, and 9.17 min from arrival of the solution to the collection tube. The corresponding solution temperatures upon injection to the blood sample were 16.4, 5.8, 2.9, 2.1, and 1.7° C. The signal of hyperpolarized [$^{15}$N]nitrate was observed in the blood for 2.9, 2.2, 1.0 and 0.6 min for the first four injections (marked 1-4 in FIG. 7A). In the last injection, the signal was observed only in one spectrum (marked 5 in FIG. 7A, signal to noise ratio of 4). This experiment demonstrates the ability to store the polarization of a single hyperpolarized [$^{15}$N] nitrate dose for several injections to blood, which is made possible by the long $T_1$ outside the blood.

Figure 7B:
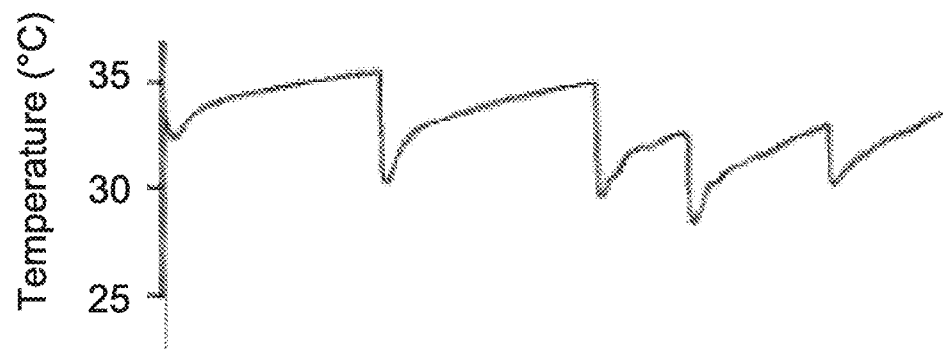
Figure 7C:
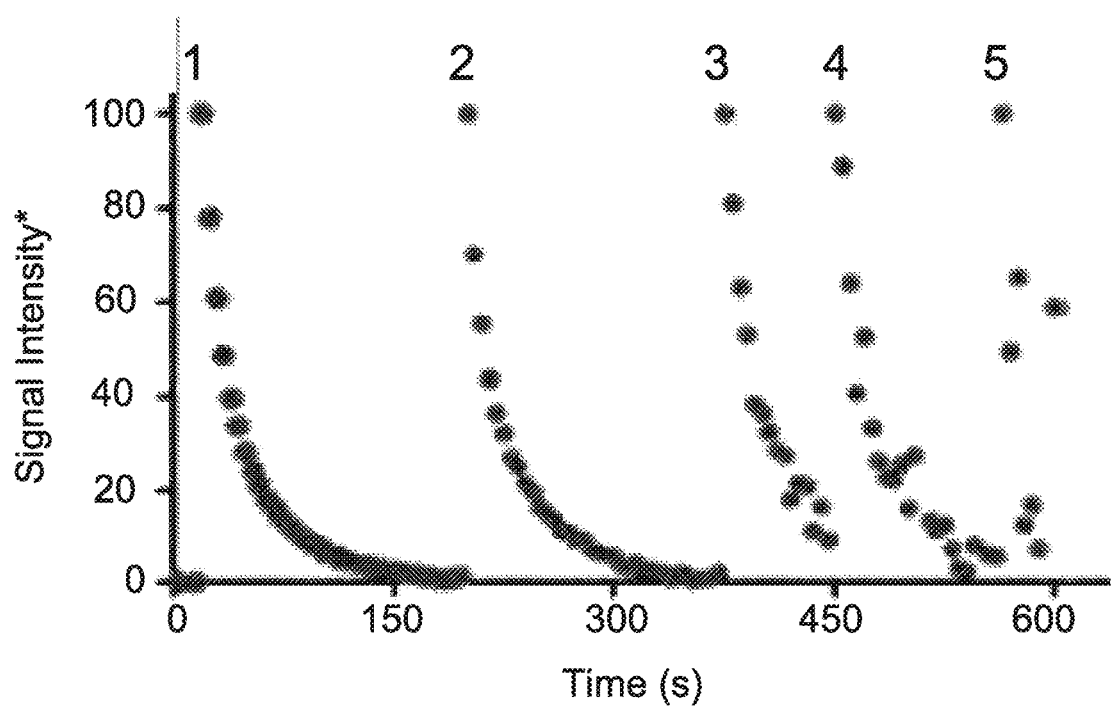
Figure 8E:
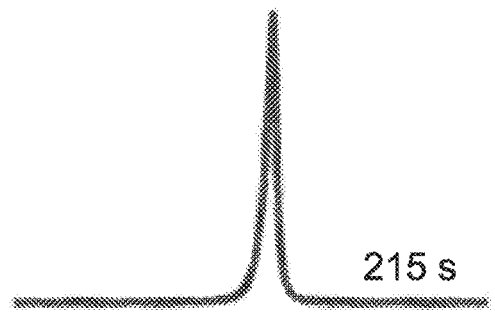
Figure 8F:
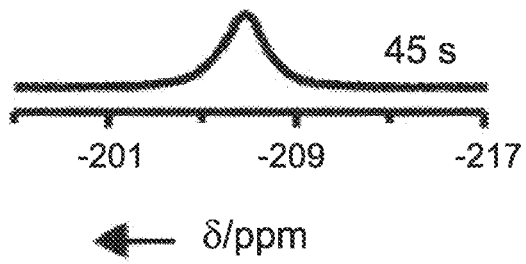
Figure 8G:
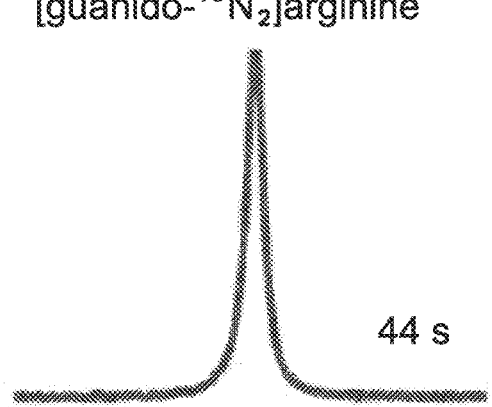
Figure 8H:
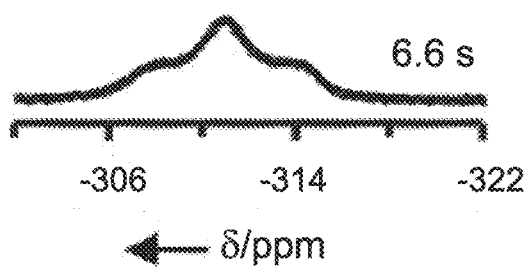

FIG. 7B shows an online temperature recording of the sample in the spectrometer. As can be seen in this figure, the injection of the hyperpolarized medium first lowers the temperature of the sample by up to 5° C., and then the temperature stabilizes. FIG. 7C shows the signal intensities of the hyperpolarized site in the consecutive injections, * indicates that the intensities are shown normalized to the highest signal for each injection.

The relative multiplication factors are 6 (decay 2), 39 (decay 3), 76 (decay 4) and 297 (decay 5). The $T_1$s in blood corresponding to the decays 1 and 2 were found to be 29±2 s and 30±3 s, respectively, the error represents the 95% confidence interval for the individual fits.

The $T_1$ of [$^{15}$N]Nitrate During the 1st and the 2nd Min of Decay in Various Solvents and Mixtures The $T_1$ of [$^{15}$N]nitrate was calculated for the 1st min (0-60 s), i.e. immediately following the injection, and for the 2nd min (65-120 s), in various experiments. In the blood-saline mixture and in four randomly selected experiments in $D_2O$ the T during the $2^d$ min was longer then the T during the 1 min. This may explain the long duration of visibility in blood and $D_2O$. In $H_2O$ and saline the $T_1$ was the same during the $1^{st}$ and at the $2^{nd}$ min of decay. However, in the saline and saliva solution the $T_1$ at the 1 min was longer than the $T_1$ for the T at $2^{nd}$ min. Thus, we conclude that the potential duration of hyperpolarized [$^{15}$N]nitrate visibility in the body of is not necessarily predictable using a monoexponential curve of the entire decay in a certain solvent or mixture.

TABLE 2

Comparison of the $T_1$ of [$^{15}$N] nitrate in the $1^{st}$ and $2^{nd}$ min of hyperpolarization decay.

| | Blood (n = 3) | $D_2O$ (n = 4*) | $H_2O$ (n = 2) | Saline (n = 1) | Saline + saliva (n = 1) |
|---|---|---|---|---|---|
| $1^{st}$ min | 27 ± 0.4 | 81 ± 20 | 99 ± 3 | 98 | 116 |
| $2^{nd}$ min | 48 ± 1 | 116 ± 7 | 99 ± 5 | 100 | 102 |

*Four measurements in $D_2O$ were randomly selected from the 12 measurements presented in Figure 1.
The data of n ≥ 1 experiments are presented as average ± standard deviation.

Discussion

As shown here, sodium [$^{15}$N]nitrate is a potential contrast agent for biomedical magnetic resonance applications in a hyperpolarized state. It is strictly water-soluble due to its ionic nature and its $T_1$ was found to be long (>100 s) compared to other water-soluble hyperpolarized sites.

This long $T_1$ appeared insensitive to the water protonation status or to salinity. However, its $T_1$ did decrease upon mixing with whole blood ($T_1$ of 29±1 s, three measurements in two different blood samples, as described in FIG. 4E and in FIG. 6C—decay 1 and 2).

On closer inspection, the $T_1$ of [$^{15}$N]nitrate in blood appeared to be prolonging with time. To test this possibility, the $T_1$ was determined in two sections of the decay data—the $1^{st}$ and the $2^{nd}$ min of the decay (0-60 s and 61-120 s, respectively). Longer $T_1$ values were found in the $2^{nd}$ min in blood (78% increase). The same trend was also observed in $D_2O$ (43% increase) but not in $H_2O$. This may be used in prolonging the visibility window of the compound in the body.

Another important factor is the stability of this compound in whole blood and saliva. The inventors could not detect any metabolism of nitrate to nitrite in the time frames investigated thus far (several minutes in blood and several hours in saliva). Therefore, these results suggest that the conversion to the reduced form is indeed low and that nitrate remains intact throughout the visualization window. In a much longer investigation of the order of several days to a month, it was able to detect conversion of [$^{15}$N]nitrate to [$^{15}$N]nitrite in two samples that contained human saliva, showing that this conversion does occur, as expected, but that this conversion is likely far from detrimental to the safety of nitrate administration.

Converting the intravenous dose previously injected in the art, which was found to be safe, to mL per min units we get 12.5 mL/min of a 0.15 M solution, which can be further converted to 6 mL/10 s of 50 mM solution. This is a routinely tolerable volume/time for human intravenous injection. A sodium nitrate solution of 50 mM is higher in concentration than the solution that was used here for consecutive injections to blood (32.6 mM). Suggesting that indeed such a safe dose of sodium [$^{15}$N]nitrate can be observed in vivo.

The non-metabolic nature of [$^{15}$N]nitrate is important in two ways: 1) in terms of safety, as nitrite is the bioactive product of nitrate, and 2) in terms of MR imaging. As for the latter, the nonmetabolic nature makes this molecular probe suitable for perfusion or tissue retention imaging.

Although many dDNP agents have been used in MR spectroscopic examinations—i.e. with the aim of demonstrating the hyperpolarized substrate metabolism—here the inventors target another MR application in which such metabolism is not desired. First, because a bioactivity is not desired, and second because a single signal is easier to image without artifacts compared to simultaneous imaging of several signals, each with different chemical shifts (in the case of nitrate and nitrite—more than 230 ppm apart). Using holding in ice-cold temperatures, outside the blood, the inventors were able to observe the hyperpolarized signal in blood for up to 9 min, using multiple injections, without any chemical modifications.

It is interesting to compare the $T_1$ of the [$^{15}$N]nitrate anion with that of the [$^{15}$N]nitrite anion. In the same solvent ($D_2O$), and in fact in the same sample, the $T_1$s of the [$^{15}$N]nitrate and the [$^{15}$N]nitrite were 100 s and 14 s, respectively. Nitric acid, $HNO_3$, is a strong acid, in contrast to nitrous acid, $HNO_2$, which is a weak acid, with a pKa of 3.15. This pKa difference may explain the $T_1$ difference: while the nitric acid is completely ionized in all solutions, the nitrous acid is in an equilibrium with the ionic form. At natural pH, most of the nitrous acid is dissociated and the anion concentration is about 4 orders of magnitude higher than the concentration of the protonated nitrous acid. Therefore, the amount of nitrous acid expected in a sodium nitrite solution is very small. However, the quickly exchanging proton (or a deuteron) on the oxygen close to nitrogen, is likely to shorten the $T_1$.

It was noted by the inventors that the polarization level achieved here for [$^{15}$N]nitrate, of 1%.

In summary, the inventors showed a novel compound for studies of dDNP hyperpolarization that may become a useful agent for MRI. The likely MRI applications appear to be imaging of blood flow in blood vessels and human tissues either normal or pathological (perfusion) and possibly, due to its ionic nature, also tissue retention—as it may linger in the extracellular space.

The $T_1$ characteristics were shown to be favorable with regard to solvent protonation and salinity, and the stability in body fluids was observed by NMR, in agreement with a previous safety study for a similar dose.

Example 3: Long-Lived $^{15}$N Hyperpolarization and Rapid Relaxation as a Potential Basis for Repeated First Pass Perfusion Imaging—Marked Effects of Deuteration and Temperature Materials and Methods

[$^{15}$N$_2$]urea and [$^{15}$N]succinimide and 99.9% $D_2O$ and glycerol were purchased from Sigma-Aldrich (Rehovot, Israel), L-[guanido-$^{15}$N$_2$]arginine:HCl and [$^{15}$N]ammonium chloride were purchased from Cambridge Isotopes Laboratories (Andover, Mass., USA).

The OXO63 radical (GE Healthcare, UK) was obtained from Oxford Instruments Molecular Biotools (Oxford, UK).

In a typical formulation the $^{15}$N labeled substrate was dissolved in a 7:3 (w/w) mixture of $D_2O$:glycerol and OXO63 radical was added to a final concentration of 13-16 mM.

Spin polarization and fast dissolution were carried out in a dDNP commercial device (HyperSense, Oxford Instruments Molecular Biotools, Oxford, UK). The sample was maintained at 1.4-1.5 K and was irradiated at 94.110 GHz. $^{15}$N NMR spectroscopy was performed in a 5.8 T NMR spectrometer (RS2D, Mundolsheim, France), using a 10-mm broadband NMR probe. The temperature in the NMR tube was continuously monitored using an NMR compatible temperature probe (Osensa, Burnaby, BC, Canada). Spectral processing and calculation of integrated intensities was performed using MNova (Mestrelab Research, Santiago de Compostela, Spain). Liquid state polarization was determined by comparing the integrated intensity of the first hyperpolarized spectrum to the integrated intensity of a standard containing a known concentration of $^{15}$N label, where the thermal equilibrium polarization is given as $Pol_{TE}=\tanh(\hbar\gamma B/2k_bT)$ Determination of the $T_1$ of the hyperpolarized sites was performed by curve fitting of the signal decay to the following equation: $S(t)=S_0 \cdot e^{-t/T_1} \cdot (\cos\theta)^{t/TR}$ in which TR, the time between excitations, and $\theta$, the nutation angle of excitation, are known. For measurements of $T_1$ in whole blood, 5.5 ml of whole blood in heparinized tube was obtained from a healthy volunteer and maintained at 20° C. for 2.5 h. Ten minutes before dissolution of the hyperpolarized urea sample, the blood was loaded into a NMR tube in the spectrometer and maintained at 36° C. The hyperpolarized urea sample was dissolved into a container outside the magnet and was injected in 0.5-1.0 mL aliquots followed by ≈2 ml of air through a tube at the bottom of the sample, to ensure no sample remained in the inlet line and complete mixing of the freshly injected solution with the blood. The sample was visually inspected at the end of the experiment to confirm that the hyperpolarized solution was well mixed with the blood and that there was no separation of the blood. Curve fitting was performed using Matlab (Mathworks, Natick, Mass., USA). Statistical analysis was performed using Microsoft Excel (Microsoft, Ra'anana, Israel).

Results

A concentrated glassing solution of [$^{15}$N$_2$]urea doped with OXO63 radical was polarized by microwave irradiation at 1.4-1.5 K (see Experimental Section). Based on measurements of the liquid state polarization observed after varying irradiation times in the solid-state, the maximum polarization of [$^{15}$N$_2$]urea was determined to be 5.1±1.6% with a buildup time of 2.3±1.2 h ($R^2$=0.93).

FIG. 8 shows $T_1$s, noted on the right of each spectrum, that were determined by fitting the hyperpolarized decay curve, correcting for the effect of repeated excitations; for each species in each solvent two measurements were performed. The spectra were normalized by the integrated intensity of the peak to emphasize the differences in line shape and chemical shift due to the different magnetic properties of the two hydrogen isotopes.

Upon dissolution of hyperpolarized [$^{15}$N$_2$]urea in $H_2O$ at ≈37° C. the $^{15}$N site showed a $T_1$ of 33±5 s (n=2). When the same sample was dissolved at the same conditions in $D_2O$, a $T_1$ of 200±20 s (n=2) was measured, corresponding to a 6.1-fold prolongation (FIGS. 8A and 8B).

In order to investigate the molecular basis for such marked differences between the effect of deuteration of exchangeable protons on the T prolongation, the inventors measured for [$^{15}$N$_2$]urea and for [$^{15}$N-amido]glutamine [13a], and examined several other molecules that also contain $^{15}$N sites bound to labile protons: [$^{15}$N]ammonium chloride, [$^{15}$N]succinimide, and [guanido-$^{15}$N$_2$]arginine (Scheme 1 above).

By comparison of the $^{15}$N spectra observed for the different molecules upon dissolution in $D_2O$ (FIGS. 8A, 8C, 8E and 8G) and $H_2O$ (FIGS. 8B, 8D, 8F and 8H) it could be seen that upon dissolution in $D_2O$ there is a shift to lower chemical shifts, as well as changes in the $^{15}$N line shape reflecting the different scalar coupling between $^{15}$N and protons and deuterons. This indicates that exchange of labile protons bound to the hyperpolarized $^{15}$N sites reaches isotopic equilibrium by the end of the ~5 s dissolution and transfer process. Therefore, it can be assumed, that differences in $T_1$s measured for the different molecules upon dissolution in $D_2O$ and $H_2O$ are not determined by the rate of hydrogen exchange.

For hyperpolarized [$^{15}$N]ammonium chloride, it was found a $T_1$ of 46±4 s (n=2) upon dissolution in $H_2O$ and 150±20 s (n=2) upon dissolution in $D_2O$ (FIGS. 8C and 8D), corresponding to a 3.3-fold $T_1$ prolongation due to deuteration of labile protons. As all protons of both urea and ammonium exchange with the solvent and the molecules are completely deuterated upon dissolution in $D_2O$, the inventors were interested in understanding if such long $T_1$s could be obtained with molecules containing also non-exchanging protons in addition to the labile protons. For this purpose, the inventors hyperpolarized [$^{15}$N]succinimide, as after dissolution in $D_2O$ only the proton directly bound to the $^{15}$N site will be exchanged to a deuteron while the four protons located three bonds away from the $^{15}$N site will not; in this case the $T_1$ in $H_2O$ was long, 45±3 s (n=2), and dissolution in $D_2O$ increased the $T_1$ to 215±2 s (n=2), corresponding to a 4.8-fold prolongation.

Thus, the presence of non-exchanging protons in the molecule is not sufficient to explain the shorter $T_1$ of [$^{15}$N-amido]glutamine.

It was hypothesized by the inventors that the symmetry and/or rigidity of the [$^{15}$N]succinimide—contributes to this longer $T_1$, despite the presence of non-exchanging protons. To measure the effect of deuteration in a non-symmetric, non-rigid small molecule, we measured the T of hyperpolarized [guanido-$^{15}$N$_2$]arginine. In this case, the inventors observed a $T_1$ of 6.6±0.3 s in $H_2O$ (n=2) and 44±1 s in $D_2O$ (n=2), corresponding to a 6.7-fold $T_1$ prolongation. These values of $T_1$ are similar to what was observed for [$^{15}$N-amido]glutamine [13a], a molecule that is also non-symmetric and non-rigid.

To summarize these measurements, it can be seen that dissolution in $D_2O$ results in long $T_1$s (>2 min) for protonated $^{15}$N sites in symmetric molecules where all protons in the molecule exchange with the solvent, i.e. [$^{15}$N$_2$]urea and [$^{15}$N]ammonium chloride. Of the three remaining molecules that contain non-exchanging protons as well as exchanging protons only [$^{15}$N]succinimide had a similarly long $T_1$ upon dissolution in $D_2O$. This may be attributable to the more symmetric structure of succinimide as compared to the more flexible structures of [$^{15}$N-amido]glutamine and [guanido-$^{15}$N$_2$]arginine, resulting in less relaxation due to $^{15}$N Chemical Shift Anisotropy (CSA) and possibly also less interaction with the non-exchanging protons due to the rigidity of the succinimide structure. Furthermore, the relative increase in $T_1$ upon deuteration of exchangeable protons varied from ≈3-7 fold. No correlation was found between the number of bound protons exchanged and the relative $T_1$ prolongation factor (R=−0.47).

However, the inventors observed that the two largest $T_1$ prolongation factors were observed for [$^{15}$N$_2$]urea and [guanido-$^{15}$N$_2$]arginine; for both of these molecules upon dissolution in $D_2O$ not only do the protons directly bound to a single $^{15}$N site exchange with deuterons but also nearby protons exchange; for [$^{15}$N$_2$]urea this means the protons bonded to the other $^{15}$N site (Scheme 1). This may explain the larger relative increase in $T_1$ in these molecules.

Figure 9A:
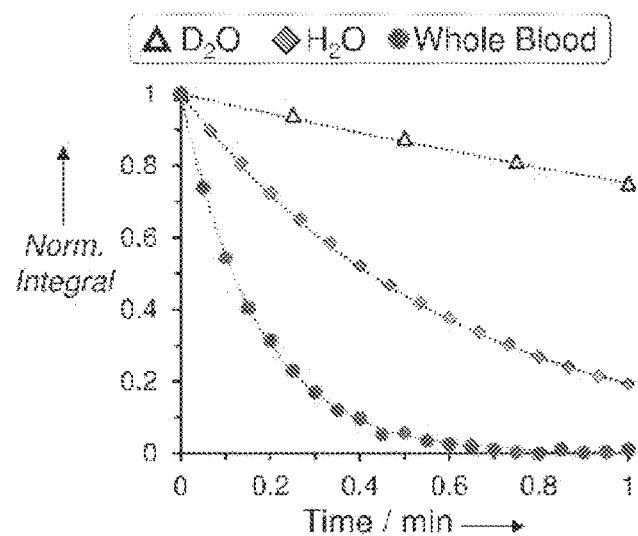
FIGS. 9A-9B hyperpolarized [$^{15}$N$_2$]urea signal.
Figure 9B:
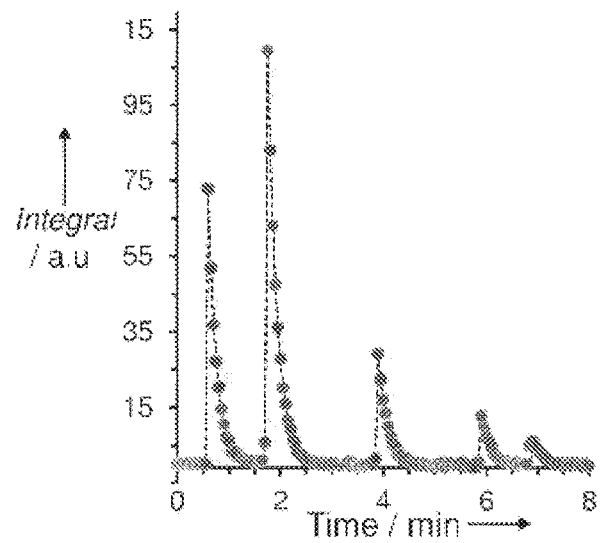

In order to utilize [$^{15}$N$_2$]urea as a hyperpolarized perfusion marker it is important to characterize its $T_1$ in whole blood. When a small amount of hyperpolarized [$^{15}$N$_2$]urea dissolved in $D_2O$ was added to whole human blood, the inventors observed a decrease in the T of the $^{15}$N site to 9.8±0.2 s (95% CI, FIG. 9A). By comparison to the decay of hyperpolarized [$^{15}$N$_2$]urea in $H_2O$ (FIG. 9A), it can be seen that the shortening of $T_1$ in the blood is not only due to protonation of the $^{15}$N site, but may also be attributed to interactions between urea and components in the blood. Despite this short lifetime of the hyperpolarized state in the blood, a single hyperpolarized dose of [$^{15}$N$_2$]urea can be observed in the blood for more than six minutes, when the hyperpolarized [$^{15}$N$_2$]urea is stored in a deuterated solution and is added in small aliquots FIG. 9B. Furthermore, it can be seen that due to the marked difference between the $T_1$ of [$^{15}$N$_2$]urea in the deuterated solution and whole blood, negligible background signal from previous injections is observed for injections separated by less than one minute (FIG. 9B). This result may serve as a basis for utilizing hyperpolarized [$^{15}$N$_2$]urea as a perfusion contrast agent as it can be injected multiple times with the background signal remaining very low for each consecutive injection.

Although the $T_1$ of [$^{15}$N$_2$]urea in whole blood is short, it can be observed for more than 6 minutes when it is stored in $D_2O$ and repeatedly added in small volumes. The $T_1$ of [$^{15}$N$_2$]urea in whole blood was determined to be 9.8±0.2 s based on the first decay curve, where the ratio of $D_2O$:whole blood was 1:10. In subsequent measurements, the measured $T_1$ increases ($2^{nd}$: $T_1$=12.0±0.2 s, $3^{rd}$: $T_1$=12.9±0.6 s etc.), an effect that can be attributed to the increasing fraction of $D_2O$ and/or dilution of the blood.

Figure 10A:
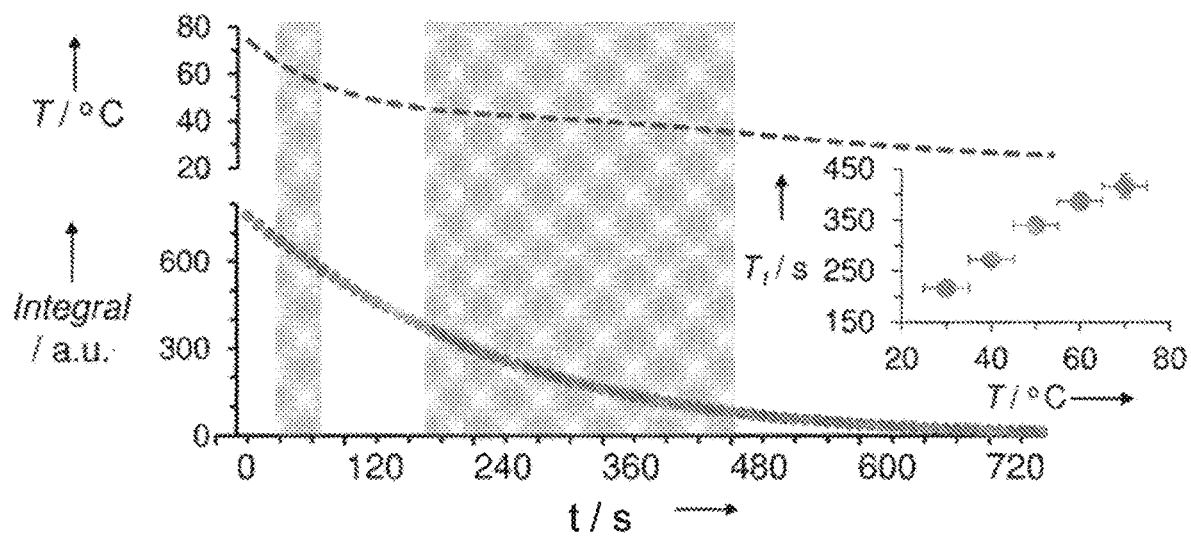
FIGS. 10A-10B hyperpolarized [$^{15}$N$_2$]urea signal.

The experiment shown in FIG. 9B clarified the importance of maximizing the $T_1$ of [$^{15}$N$_2$]urea for optimal storage of the polarization, in order to expand the time scale in which the hyperpolarized signal from a single dose can be observed in vivo. As for storage there are no limitation to physiological temperatures, the effect of temperature on the $T_1$ of [$^{15}$N$_2$]urea was measured. Given the impressive signal afforded by the dDNP process and its long lifetime, it was possible to measure the $T_1$ of the $^{15}$N sites of urea for a range of temperatures with a single sample that was slowly heated or cooled while the temperature was continuously monitored with an NMR compatible temperature probe (FIG. 10A, top). In order to determine the temperature dependent $T_1$, the decay data were retrospectively binned to consecutive 10° C. segments (FIG. 10A, alternating shading indicates different 10° C. segments) and the T for each temperature segment was determined (FIG. 10B, inset).

The hyperpolarized decay acquisitions were carried out with 3-10° excitation angle and 5-20 s repetition time. There was no significant difference in the T determined with different acquisition parameters.

Figure 10B:
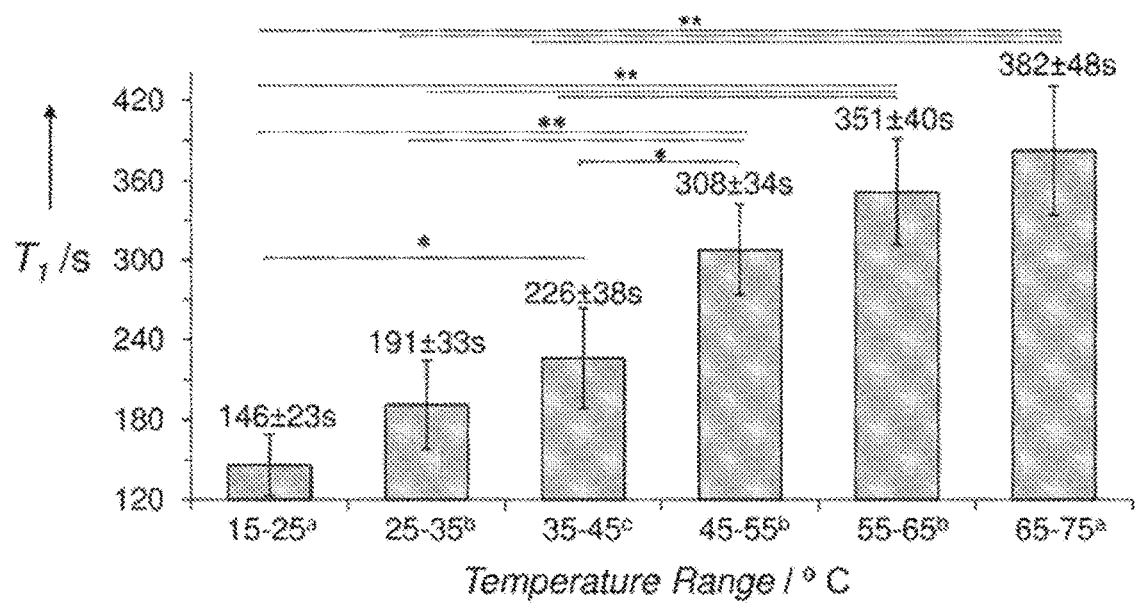

In total, 24 segments were fit from ten different samples and the results are presented in FIG. 10B. It can be observed that at higher temperatures the $T_1$ of the $^{15}$N sites of [$^{15}$N$_2$]urea was longer, reaching more than 6 min at 65-75° C. (FIG. 10B). Due to technical limitations it was not possible to reach higher sample temperatures, however it seems likely that further increasing the temperature will further increase the $T_1$.

Here, it was demonstrated that for the protonated primary and secondary amines [$^{15}$N]ammonium, [$^{15}$N$_2$]urea, and [$^{15}$N]succinimide, long $T_1$s can be observed by deuteration of the exchangeable protons. Specifically, it was demonstrated that upon dissolution of [$^{15}$N$_2$]urea hyperpolarized by dDNP in deuterated water at physiological temperatures a $T_1$ in excess of 3 min is observed and by heating the hyperpolarized solution to temperatures above 65° C. the $T_1$ can be further prolonged to more than 6 min. This long $T_1$ will potentially ensure that the high level of solid state polarization will be well preserved during the 1 min required for transfer and administration of the hyperpolarized dose in the clinical setting; there will only be a ≈25% decrease in the [$^{15}$N$_2$]urea polarization if the entire process occurs at physiological temperatures, and a much smaller decrease if some of the steps could be performed at higher temperatures, with the sample cooled to 37° C. only immediately prior to injection. By contrast, the same interval will result in ≈80% reduction of the polarization if the carbon-13 labeled urea is used ($T_1$≈40 s in solution).

The in vivo $T_1$ of [$^{15}$N$_2$]urea will be significantly shortened due to protonation of the $^{15}$N sites by chemical exchange with $H_2O$ in vivo and due to relaxation of the $^{15}$N magnetization by interactions with components in the blood; indeed, a $T_1$ of 10 s was found here for hyperpolarized [$^{15}$N$_2$]urea in whole blood at 37° C. The protonation of deuterated [$^{15}$N$_2$]urea in vivo can also be advantageous if it can be exploited to efficiently transfer polarization from the hyperpolarized $^{15}$N sites to the directly bound protons, corresponding to a ≈100-fold more sensitive detection than direct $^{15}$N detection. The efficiency of this polarization transfer will be determined by the lifetime of the urea proton in vivo.

In this work the inventors have focused on hyperpolarization of $^{15}$N by dDNP. Despite the advantages of $^{15}$N hyperpolarization by SABRE, unlike dDNP, such high levels of polarization have not been achieved in the biocompatible solvents safe for in vivo imaging applications

TABLE 3

T₁ of [$^{15}N_2$] urea as determined when measured with various flip angles (θ) and repetition times (TR).

| | #1 | #2 | #3 | #4 | #5 | #6 | #7 | #8 | #9 | #10 | Average ± SD |
|---|---|---|---|---|---|---|---|---|---|---|---|
| θ (°) | 10° | 3° | 10° | 10° | 10° | 10° | 10° | 10° | 5° | 10° | |
| TR (s) | 5 | 10 | 10 | 10 | 10 | 10 | 15 | 15 | 20 | 10 | |
| 15-25° C. | | 155 ± 3 | | | | 112 ± 6 | | | 163 ± 20 | | 146 ± 23 (n = 3) |
| 25-35° C. | | 196 ± 8 | 209 ± 2 | 216 ± 2 | | 143 ± 1 | | | | | 191 ± 33 (n = 4) |
| 35-45° C. | 228 ± 4 | | 266 ± 4 | 272 ± 3 | 216 ± 5 | | 198 ± 2 | 176 ± 5 | | | 226 ± 38 (n = 6) |
| 45-55° C. | | | 355 ± 8 | 340 ± 5 | 273 ± 4 | | | | 284 ± 6 | | 308 ± 34 (n = 4) |
| 55-65° C. | | | 382 ± 17 | 386 ± 12 | 305 ± 14 | | | | 332 ± 11 | | 351 ± 40 (n = 4) |
| 65-75° C. | | | | 416 ± 23 | 327 ± 16 | | | | 404 ± 41 | | 382 ± 48 (n = 3) |

Individual measurements are shown. Each column represents a single hyperpolarized decay, obtained with the same flip angle and repetition time. Using an online measurement of the temperature inside the NMR tube, we could differentiate different temperature regimes within a single decay and thus assess the effect of temperature on $T_1$. $T_1$ values were determined by fitting the equation describing the mono-exponential decay of a hyperpolarized signal: $S(t)=S0 \cdot e-t/T1 \cdot (\cos \theta)t/TR$.

The angle of excitation was determined by calibration of the 90o excitation on a $^{15}$N labeled standard. The error for each individual measurement represents the 95% confidence interval of the curve fit.

The temperature gradient was formed by adding a solution at a temperature different than the spectrometer temperature so that throughout the acquisition the sample slowly cooled/warmed to the spectrometer temperature. It appears that the stronger excitation schemes (shaded in dark grey) did not result in different values of $T_1$ compared to the more weak excitation schemes (shaded in light grey). Variability in the determined $T_1$ values may be due to slight variations in the effective angle of excitation and/or the amount of trace protons present in different samples; indeed when different temperature segments are compared within the same hyperpolarized decay, (i.e. for the same sample on the same day), the dependence of $T_1$ on the temperature can be even more clearly seen. The average and standard deviation of all measurements in the same temperature regime are shown in the column on the right.

Conclusions

It was suggested by the inventors that hyperpolarized [$^{15}N_2$]urea is a promising marker for first-pass perfusion imaging, for which the relevant time scales in vivo are shorter and the marked difference between the $T_1$ in the deuterated dissolution media and in vivo is advantageous, as it is possible to capitalize on it to perform repeated first-pass perfusion measurements from a single hyperpolarized solution with negligible background signal from previous injections; such an ability is desirable either for improving the accuracy of the first-pass perfusion measurement and/or for investigation of changes in perfusion in response to fast-acting pharmaceutical challenges.

Example 4: Diagnosis of Breast Cancer Using N15-Labeled Nitrate 50 mM solution of hyperpolarized [$^{15}$N]nitrate is injected to a breast tumor bearing mouse. $^{15}$N MR imaging is performed following the administration of the solution to the mouse. The mouse vascular system is enhanced in the MR image. The tumor tissue is enhanced in the MR image due to the enhanced-permeability-and-retention effect in the tumor tissue.

The invention claimed is:

1. A method of diagnosis a condition or disease in a subject, the method comprising administrating to the subject a diagnostically effective amount of at least one hyperpolarized labeled compound comprising at least one isotopically labeled nitrogen atom and monitoring a signal from the hyperpolarized compound in the subject, to thereby diagnose the condition or disease in the subject, optionally the signal is monitored by magnetic resonance techniques, wherein the hyperpolarized labeled compound is Na[$^{15}$N] nitrate and optionally comprises at least one isotopically labeled hydrogen atom.

2. The method according to claim 1, wherein the monitoring is by acquiring at least one $^1$H and/or at least one $^2$H and/or at least one $^{15}$N magnetic resonance (MR) spectrum and/or image from the subject's body or any one or more regions thereof.

3. The method according to claim 1, comprising prior to the administration step, acquiring at least one $^1$H, $^2$H or $^{15}$N MR spectrum and/or image from the subject's body or any one or more regions thereof.

4. The method according to claim 3, comprising comparing at least one parameter obtained from the at least one $^1$H, $^2$H or $^{15}$N MR spectrum and/or image to at least one parameter obtained from the at least one $^1$H, $^2$H or $^{15}$N MR spectrum and/or image in the same subject at an earlier point in time, wherein the comparison permits diagnosis of the disease.

5. The method according to claim 1, comprising prior to the administration step, a step of hyperpolarization to obtain a hyperpolarized compound in solid-state form.

6. The method according to claim 5, comprising dissolving the hyperpolarized compound in the solid-state in an aqueous solution to obtain the hyperpolarized compound, optionally the aqueous solution comprising $D_2O$.

7. The method according to claim 6, wherein the hyperpolarized compound is administrated to the subject at a time period of between 10 seconds to 240 seconds after dissolving the compound in the aqueous solution.

8. The method according to claim 1, wherein the hyperpolarized labeled compound is characterized by least 5% to 50% increased polarization compared to the same compound in a non-hyperpolarized state.

9. The method according to claim 1, wherein the hyperpolarized labeled compound has a $T_1$ relaxation of a $^{15}N$ nucleus of between about 30 seconds to about 10 minutes.

10. The method according to claim 1, wherein the condition or disease is selected from oncology, neurology, psychiatry, cardiology, vascular, infection and inflammation.

11. The method according to claim 1, wherein the condition is a proliferative disorder.

\* \* \* \* \*